(12) United States Patent
Thompson

(10) Patent No.: US 7,974,685 B2
(45) Date of Patent: Jul. 5, 2011

(54) SYSTEMS, DEVICES, AND METHODS FOR TACHYARRHYTHMIA DISCRIMINATION OR THERAPY DECISIONS

(75) Inventor: Julie Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 946 days.

(21) Appl. No.: 11/751,769

(22) Filed: May 22, 2007

(65) Prior Publication Data

US 2007/0219456 A1    Sep. 20, 2007

Related U.S. Application Data

(63) Continuation-in-part of application No. 10/897,365, filed on Jul. 22, 2004, now Pat. No. 7,228,176.

(51) Int. Cl.
    *A61B 5/04* (2006.01)
(52) U.S. Cl. .......... 600/509; 600/513; 600/515
(58) Field of Classification Search .......... 600/509, 600/513, 515
    See application file for complete search history.

(56) References Cited

U.S. PATENT DOCUMENTS

| | | | |
|---|---|---|---|
| 4,485,818 A * | 12/1984 | Leckrone et al. .......... 607/9 |
| 4,830,006 A | 5/1989 | Haluska et al. |
| 5,002,052 A | 3/1991 | Haluska |
| 5,107,850 A | 4/1992 | Olive |
| 5,161,527 A | 11/1992 | Nappholz et al. |
| 5,193,550 A | 3/1993 | Duffin |
| 5,205,283 A | 4/1993 | Olson |
| 5,301,677 A | 4/1994 | Hsung |
| 5,873,897 A | 2/1999 | Armstrong et al. |
| 5,891,170 A | 4/1999 | Nitzsche et al. |
| 5,951,592 A | 9/1999 | Murphy |
| 5,978,707 A | 11/1999 | Krig et al. |
| 6,108,578 A | 8/2000 | Bardy et al. |
| 6,151,524 A | 11/2000 | Krig et al. |
| 6,178,350 B1 | 1/2001 | Olson et al. |
| 6,179,865 B1 * | 1/2001 | Hsu et al. .......... 600/518 |

(Continued)

FOREIGN PATENT DOCUMENTS

EP    253505    1/1988

(Continued)

OTHER PUBLICATIONS

"International Search Report and Written Opinion for Application No. PCT/US/2005/025397, date mailed Mar. 22, 2006", 21 Pages.

(Continued)

*Primary Examiner* — Carl H Layno
*Assistant Examiner* — Natasha N Patel
(74) *Attorney, Agent, or Firm* — Schwegman, Lundberg & Woessner, P.A.

(57) ABSTRACT

Systems, devices, and methods detect or classify tachyarrhythmias or make a therapy decision. A tachyarrhythmia can be classified using a rhythm discrimination parameter having a value. In certain examples, the value of the rhythm discrimination parameter can be adjusted using a relationship between a detected atrial rate and a detected ventricular rate, or the value can be adjusted using information about at least one of the atrial rate or the ventricular rate in addition to using the relationship between the atrial rate and the ventricular rate. These techniques can improve the specificity of arrhythmia detection or classification, allow anti-tachyarrhythmia therapy to be better tailored to the particular tachyarrhythmia, or provide more automatic operation making it easier for a physician to use an implantable device.

27 Claims, 14 Drawing Sheets

U.S. PATENT DOCUMENTS

| | | |
|---|---|---|
| 6,230,055 B1 | 5/2001 | Sun et al. |
| 6,275,732 B1 | 8/2001 | Hsu et al. |
| 6,317,632 B1 | 11/2001 | Krig et al. |
| 6,484,055 B1 | 11/2002 | Marcovecchio |
| 6,493,579 B1 | 12/2002 | Gilkerson et al. |
| 6,516,225 B1 | 2/2003 | Florio |
| 6,658,286 B2 | 12/2003 | Seim |
| 6,671,548 B1 | 12/2003 | Mouchawar et al. |
| 7,228,176 B2 | 6/2007 | Smith et al. |
| 7,386,344 B2 * | 6/2008 | Bocek et al. .................. 607/5 |
| 7,797,037 B2 * | 9/2010 | Elahi et al. .................. 600/518 |
| 2002/0035335 A1 | 3/2002 | Schauerte |
| 2002/0143370 A1 | 10/2002 | Kim |
| 2002/0147407 A1 | 10/2002 | Seim |
| 2002/0147474 A1 | 10/2002 | Seim et al. |
| 2005/0149125 A1 | 7/2005 | Kim et al. |
| 2005/0256544 A1 | 11/2005 | Thompson |
| 2006/0074330 A1 * | 4/2006 | Smith et al. .................. 600/515 |
| 2006/0281998 A1 | 12/2006 | Li |

FOREIGN PATENT DOCUMENTS

| | | |
|---|---|---|
| EP | 360412 | 3/1990 |
| EP | 469817 | 2/1992 |
| EP | 597459 | 5/1994 |
| EP | 0597459 A2 | 5/1994 |
| EP | 744190 | 11/1996 |
| EP | 0744190 | 11/1996 |
| EP | 0879621 A2 | 11/1998 |
| EP | 919256 | 6/1999 |
| EP | 993842 | 4/2000 |
| EP | 1112756 | 7/2001 |
| WO | WO-9739799 | 10/1997 |
| WO | WO-9825669 | 6/1998 |
| WO | WO-9848891 | 11/1998 |
| WO | WO-9915232 | 4/1999 |
| WO | WO-0053089 | 9/2000 |
| WO | WO-0059573 | 10/2000 |
| WO | WO-0113993 | 3/2001 |
| WO | WO-03047690 | 6/2003 |
| WO | WO-2006020198 A2 | 2/2006 |

OTHER PUBLICATIONS

"Invitation to Pay Additional Fees for application No. PCT/US2005/025397, date mailed Dec. 16, 2005", 8 pages.

"Non-Final Office Action mailed by the USPTO on Oct. 27, 2006 for related matter U.S. Appl. No. 10/897,365", 14 Pages.

"Notice of Allowance mailed by the USPTO on Feb. 2, 2007 for related matter U.S. Appl. No. 10/897,365", 9 Pages.

Medtronic, "Marquis DR 7274 Dual Chamber Implantable Cardioverter Defibrillator", Reference Manual,(Feb. 2002),426 pgs.

"U.S. Appl. No. 10/897,365, Amendment and Response filed Dec. 8, 2006 to Non-Final Office Action mailed Oct. 27, 2006", 17 pgs.

"U.S. Appl. No. 10/897,365, Non-Final Office Action mailed Oct. 27, 2006", 7 pgs.

"U.S. Appl. No. 10/897,365, Notice of Allowance mailed Feb. 2, 2007", 8 pgs.

"International Application Serial No. PCT/US2008/006393, International Search Report mailed Aug. 20, 2008", 6 pgs.

"International Application Serial No. PCT/US2008/006393, Written Opinion mailed Aug. 20, 2008", 8 pgs.

* cited by examiner

SYSTEMS, DEVICES, AND METHODS FOR TACHYARRHYTHMIA DISCRIMINATION OR THERAPY DECISIONS

CROSS-REFERENCE TO RELATED APPLICATIONS

This application is a continuation-in-part of U.S. patent application Ser. No. 10/897,365, now issued as U.S. Pat. No. 7,228,176, filed on Jul. 22, 2004 which is hereby incorporated by reference in their entirety.

TECHNICAL FIELD

This patent application pertains generally to cardiac rhythm management and more particularly, but not by way of limitation, to systems and methods for classifying a tachyarrhythmia.

BACKGROUND

Implantable medical devices include, among other things, cardiac rhythm management (CRM) devices such as pacers, cardioverters, defibrillators, cardiac resynchronization therapy (CRT) devices, as well as combination devices that provide more than one of these therapy modalities to a patient. For example, a tachyarrhythmia includes a too-fast heart rhythm. A tachyarrhythmia may be caused by an improper positive-feedback-like reentry of intrinsic electrical signals that control heart contractions. A tachyarrhythmia may result in inefficient pumping of blood. Fibrillation is a particularly severe tachyarrhythmic episode. While ventricular fibrillation ("VF") can have immediate life-threatening consequences, the adverse effects of atrial fibrillation ("AF") are typically less immediate or severe. Atrial tachyarrhythmias (i.e., "AT"s, including AF) may call for a different therapy than ventricular tachyarrhythmias (i.e., "VT"s). For example, a VF may call for delivering a painful defibrillation shock to interrupt the VF, while an AF may call for delivering a painless anti-tachyarrhythmia pacing to interrupt the AF. Therefore, to promote efficacy or patient comfort, it is useful to know whether a particular tachyarrhythmia originates in the ventricle (i.e., is a VT) or above the ventricle (i.e., is a supraventricular tachyarrhythmia ("SVT"), such as an AT).

However, it is sometimes difficult to know where the tachyarrhythmia originates. A SVT may conduct its too-fast heart rhythm through the atrioventricular (AV) node to the ventricle, resulting in a fast ventricular heart rate. Similarly, a VT may exhibit retrograde conduction of its too-fast heart rhythm back to the atrium, resulting in a fast atrial heart rate. Thus, discriminating between the different origins of VTs and SVTs may not be an easy task. Accomplishing this VT/SVT discrimination task may require a physician to program a complicated set of parameters to achieve the intended result. The present inventors have recognized an unmet need for automatically or otherwise providing improved sensitivity and specificity of discriminating between VTs and SVTs, such as to avoid unneeded defibrillation shocks and to more effectively treat the particular tachyarrhythmia.

Overview

This overview is intended to provide an overview of the subject matter of the present patent application. It is not intended to provide an exclusive or exhaustive explanation of the invention. The detailed description is included to provide further information about the subject matter of the present patent application.

Systems, devices, and methods detect or classify tachyarrhythmias or make a therapy decision. A tachyarrhythmia can be classified using a rhythm discrimination parameter having a value. In certain examples, the value of the rhythm discrimination parameter can be adjusted using a relationship between a detected atrial rate and a detected ventricular rate, or the value can be adjusted using information about at least one of the atrial rate or the ventricular rate in addition to using the relationship between the atrial rate and the ventricular rate. These techniques can improve the specificity of arrhythmia detection or classification, allow anti-tachyarrhythmia therapy to be better tailored to the particular tachyarrhythmia, or provide more automatic operation making it easier for a physician to use an implantable device.

In Example 1, a system includes an atrial contraction detector circuit, including an atrial rate detector circuit to detect an atrial rate between atrial contractions of a heart, a ventricular contraction detector circuit, including a ventricular rate detector circuit to detect a ventricular rate between ventricular contractions of the heart, a tachyarrhythmia classification circuit configured to classify a tachyarrhythmia using a rhythm discrimination parameter having a value, and a processor, the processor configured to be coupled to the atrial and ventricular contraction detector circuits and the tachyarrhythmia classification circuit, the processor configured to adjust the value of the rhythm discrimination parameter using a relationship between the atrial rate and the ventricular rate.

In Example 2, the relationship between the atrial rate and the ventricular rate of Example 1 optionally includes information about the amount that the ventricular rate exceeds the atrial rate.

In Example 3, the processor of Examples 1-2 is optionally configured to adjust the value of the rhythm discrimination parameter using at least one of the atrial rate or the ventricular rate in addition to using the relationship between the atrial rate and the ventricular rate.

In Example 4, the processor of Examples 1-3 is optionally configured to adjust the value of the rhythm discrimination parameter using information about the amount that the ventricular rate exceeds the atrial rate as a function of at least one of the atrial rate or the ventricular rate.

In Example 5, the processor of Examples 1-4 is optionally configured to adjust the value of the rhythm discrimination parameter using information about whether the ventricular rate exceeds the atrial rate by a threshold value, wherein the threshold value varies as a function of at least one of the atrial rate or the ventricular rate.

In Example 6, the atrial rate of Examples 1-5 is optionally represented by an atrial interval between atrial contractions, and the ventricular rate of Examples 1-6 is optionally represented by a ventricular interval between ventricular contractions.

In Example 7, the tachyarrhythmia classification circuit of Examples 1-6 optionally includes a comparator configured to compare information from at least one of the atrial contraction detector circuit or the ventricular contraction detector circuit to the value of the rhythm discrimination parameter, and the tachyarrhythmia classification circuit of Examples 1-6 is optionally configured to classify the tachyarrhythmia using the results of the comparison.

In Example 8, the rhythm discrimination parameter of Examples 1-7 optionally includes at least one of stability, onset, or morphology correlation.

In Example 9, the rhythm discrimination parameter of Examples 1-8 optionally includes stability and the value of the rhythm discrimination parameter of Examples 1-8 optionally includes a variance threshold.

In Example 10, the rhythm discrimination parameter of Examples 1-9 optionally includes onset and the value of the rhythm discrimination parameter of Examples 1-9 optionally includes a rate progression threshold.

In Example 11, the ventricular contraction detector circuit of Examples 1-10 is optionally configured to detect a ventricular contraction and provide a ventricular contraction signal, and the rhythm discrimination parameter of Examples 1-10 optionally includes morphology correlation and the value of the rhythm discrimination parameter of Examples 1-10 optionally includes a morphology correlation threshold between the ventricular contraction signal and a template.

In Example 12, the template of Examples 1-11 optionally includes at least one of a normal sinus rhythm ventricular contraction template or a tachyarrhythmia ventricular contraction template.

In Example 13, the system of Examples 1-12 optionally includes a therapy delivery circuit configured to deliver an anti-tachyarrhythmia therapy if the tachyarrhythmia classification circuit of Examples 1-12 classifies the tachyarrhythmia as a ventricular tachyarrhythmia.

In Example 14, a system includes means for detecting atrial contractions of a heart and an atrial rate between the detected atrial contractions, such as by using an atrial contraction detector circuit, including an atrial rate detector circuit to detect an atrial rate between atrial contractions of a heart, and means for detecting ventricular contractions of the heart and a ventricular rate between the detected ventricular contractions, such as by using a ventricular contraction detector circuit, including a ventricular rate detector circuit to detect a ventricular rate between ventricular contractions of the heart. The system also includes means for classifying a tachyarrhythmia using a rhythm discrimination parameter having a value, such as by using a tachyarrhythmia classification circuit, and means for adjusting the value of the rhythm discrimination parameter using a relationship between the atrial rate and the ventricular rate, such as by using a processor.

In Example 15, a method includes detecting atrial contractions of a heart and an atrial rate between the detected atrial contractions and detecting ventricular contractions of the heart and a ventricular rate between the detected ventricular contractions. The method also includes classifying a tachyarrhythmia using a rhythm discrimination parameter having a value, and adjusting the value of the rhythm discrimination parameter using a relationship between the atrial rate and the ventricular rate.

In Example 16, the using the relationship between the atrial rate and the ventricular rate of Example 15 optionally includes using information about the amount that the ventricular rate exceeds the atrial rate.

In Example 17, the adjusting the value of the rhythm discrimination parameter of Examples 15-16 optionally includes using at least one of the atrial rate or the ventricular rate in addition to using the relationship between the atrial rate and the ventricular rate.

In Example 18, the adjusting the value of the rhythm discrimination parameter of Examples 15-17 optionally includes using information about the amount that the ventricular rate exceeds the atrial rate as a function of at least one of the atrial rate or the ventricular rate.

In Example 19, the adjusting the value of the rhythm discrimination parameter of Examples 15-18 optionally includes using information about whether the ventricular rate exceeds the atrial rate by a threshold value that varies as a function of at least one of the atrial rate or the ventricular rate.

In Example 20, the detecting the atrial rate of Examples 15-19 optionally includes detecting an atrial interval between atrial contractions and the detecting the ventricular rate includes detecting a ventricular interval between ventricular contractions.

In Example 21, the method of Examples 15-20 optionally includes comparing information from at least one of the detected atrial contractions or the detected ventricular contractions to the value of the rhythm discrimination parameter. The classifying the tachyarrhythmia of Examples 15-20 also optionally includes using the results of the comparison.

In Example 22, the classifying the tachyarrhythmia using the rhythm discrimination parameter of Examples 15-21 optionally includes classifying the tachyarrhythmia using at least one of stability, onset, or morphology correlation.

In Example 23, the classifying the tachyarrhythmia using the rhythm discrimination parameter having a value of Examples 15-22 optionally includes classifying the tachyarrhythmia using stability having a variance threshold.

In Example 24, the classifying the tachyarrhythmia using the rhythm discrimination parameter having a value of Examples 15-23 optionally includes classifying the tachyarrhythmia using onset having a rate progression threshold.

In Example 25, the method of Examples 15-24 optionally includes providing a ventricular contraction signal using at least one detected ventricular contraction. The classifying the tachyarrhythmia using the rhythm discrimination parameter having the value of Examples 15-24 also optionally includes using morphology correlation having a morphology correlation threshold.

In Example 26, the using morphology correlation having the morphology correlation threshold of Examples 15-25 optionally includes determining a morphology correlation value between the ventricular contraction signal and a template and comparing the determined morphology correlation value to the morphology correlation threshold.

In Example 27, the template of Examples 15-26 optionally includes at least one of a normal sinus rhythm ventricular contraction template or a tachyarrhythmia ventricular contraction template.

In Example 28, the method of Examples 15-27 optionally includes delivering an anti-tachyarrhythmia therapy if the tachyarrhythmia is classified as a ventricular tachyarrhythmia.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Systems, devices, and methods detect or classify tachyarrhythmias or make a therapy decision. A tachyarrhythmia can be classified using a rhythm discrimination parameter having a value. In certain examples, the value of the rhythm discrimination parameter can be adjusted using a relationship between a detected atrial rate and a detected ventricular rate, or the value can be adjusted using information about at least one of the atrial rate or the ventricular rate in addition to using the relationship between the atrial rate and the ventricular rate. These techniques can improve the specificity of arrhythmia detection or classification, allow anti-tachyarrhythmia therapy to be better tailored to the particular tachyarrhythmia, or provide more automatic operation making it easier for a physician to use an implantable device.

Figure 1:
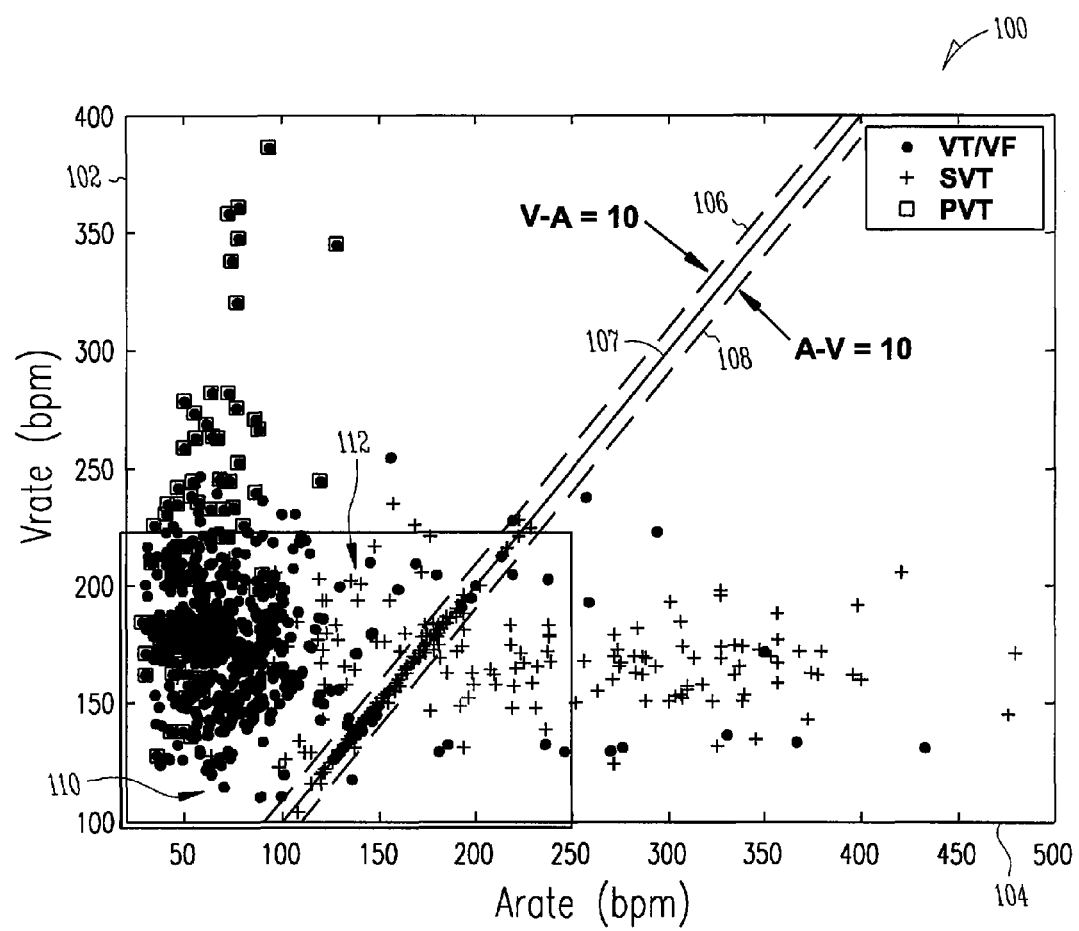
FIG. 1 is a graph of data illustrating tachyarrhythmia episodes from different patients.

FIG. 1 is a graph 100 of data illustrating tachyarrhythmia episodes from different patients, as collected and analyzed by the present inventors. The graph of FIG. 1 includes a y-axis 102 that illustrates ventricular rate (in beats per minute), and an x-axis 104 that illustrates atrial rate (in beats per minute). In FIG. 1, each VT (including VF) episode is indicated by a bullet (•) and each SVT (including AF) episode is indicated by a plus (+). Each polymorphic VT episode is illustrated by a box (□) around the corresponding bullet. A VT episode indicated by a bullet without a corresponding box is a monomorphic VT episode. A monomorphic VT episode has a more regular morphology (i.e., shape) of intrinsic heart signal than a polymorphic VT episode. A monomorphic VT episode may call for a different anti-tachyarrhythmia therapy than a polymorphic VT episode.

In FIG. 1, a line with a slope of +0.5 and intersecting the (extrapolated) y-axis 102 at y=0 defines an atrial rate ("AR") that is equal to a ventricular rate ("VR"). As seen in FIG. 1, most VT episodes correspond to VR>AR. Similarly, most SVT episodes correspond to AR>VR. Therefore, one way to distinguish between a VT episode and an SVT episode in an implantable medical device is to include an algorithm that compares AR and VR. If VR>AR by a desired threshold value (e.g., 10 bpm), then the algorithm deems the detected arrhythmia to be a VT. In FIG. 1, this corresponds to episodes to the left of line 106. In this example, if AR>VR by the same or a different threshold value (e.g., 10 bpm), then the algorithm deems the detected arrhythmia to be an SVT. In FIG. 1, this corresponds to episodes to the right of line 108. If both desired threshold values are set to zero, this reduces to classifying episodes to the left of the AR=VR line as VTs and classifying the episodes to the right of the AR=VR line as SVTs. If desired, anti-tachyarrhythmia therapy can be tailored to the particular tachyarrhythmia using this information, and delivered to the patient.

Figure 2:
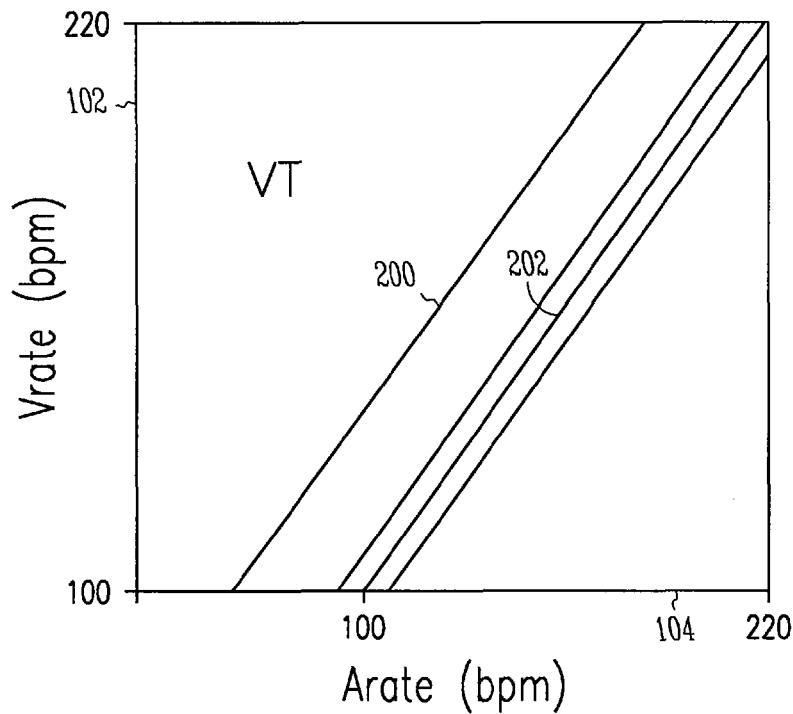
FIG. 2 is a graph illustrating conceptually one example of using a fixed rate threshold for comparing atrial and ventricular rates, such as for classifying a tachyarrhythmia as a ventricular tachyarrhythmia.

However, in FIG. 1, there are fewer VTs at lower ventricular rates, such as in region 110, than at higher ventricular rates. Also, in FIG. 1, there are fewer VTs, and more SVTs where the atrial rate exceeds an atrial rate cutoff value (e.g., at an AR that is somewhere between about 100 bpm and 200 bpm), such as in region 112. Among other things, the present inventors have recognized that using a substantially larger fixed threshold for the comparison (e.g., VR>>AR by a fixed threshold value of at least about 40 bpm to about 60 bpm, instead of the 10 bpm depicted by the line 106 in FIG. 1) would improve the specificity of classifying a tachyarrhythmia as VT. This is illustrated by the boundary line 200 in the graph of FIG. 2. The threshold value for the comparison is shown as the distance between the boundary line 200 in FIG. 2 and a VR=AR line 202 having slope=0.5 and y-intercept=0.

Moreover, the present inventors have recognized that instead of using a fixed threshold for comparing AR and VR (e.g., a threshold represented on FIG. 1 by a boundary line having a fixed distance from an AR=VR line 107 having slope of 0.5 and y-intercept of 0), using an atrial or ventricular rate dependent or other variable threshold may add power to the VT/SVT discrimination and classification algorithm, thereby improving its sensitivity or specificity.

Figure 3:
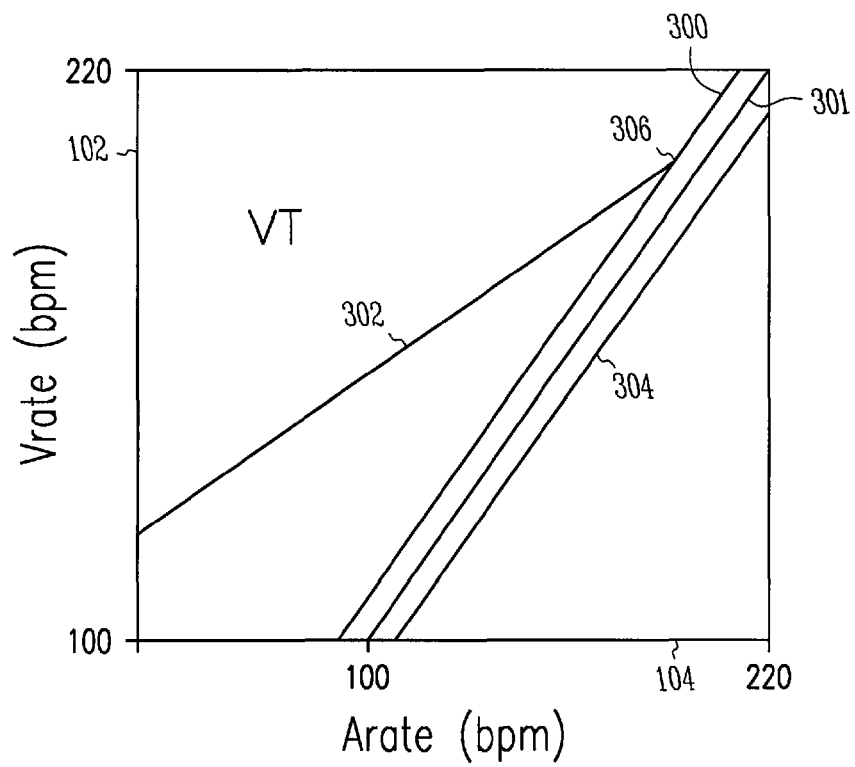
FIG. 3 is a graph illustrating a rate-dependent comparison threshold, such as illustrated by a bilinear, piecewise linear, curvilinear, or other nonlinear threshold boundary.

FIG. 3 is a graph illustrating a rate-dependent comparison threshold, such as illustrated by a bilinear, piecewise linear, curvilinear, or other nonlinear threshold boundary 300 in the context of the graph of FIG. 3. (In examples illustrated in graphs such as shown in FIG. 3, the actual threshold value for comparing AR and VR is the distance between the threshold boundary 300 and the AR=VR line 301 illustrated in FIG. 3.)

In the example of FIG. 3, the threshold boundary 300 is such that, for an arrhythmia to be classified as a VT, VR must exceed AR by a greater threshold amount at lower values of VR than at higher values of VR. In other words, the distance between the threshold boundary 300 and the AR=VR line 301 is greater at lower values of VR than at higher values of VR.

Similarly, the distance between the threshold boundary 300 and the AR=VR line 301 is greater at lower values of AR than at higher values of AR.

The example of FIG. 3 depicts a bilinear threshold boundary 300, formed by the line segments 302 and 304, which are joined at breakpoint 306. In this example, the line segment 302, at lower values of VR and AR, is rate dependent (because its slope is not equal to 0.5) and the line segment 304, at higher values of VR and AR is rate independent (because its slope is equal to 0.5). Therefore, in its entirety, the threshold boundary 300 can be considered rate dependent because at least a portion of it (i.e., line segment 302) is rate dependent.

Figure 4:
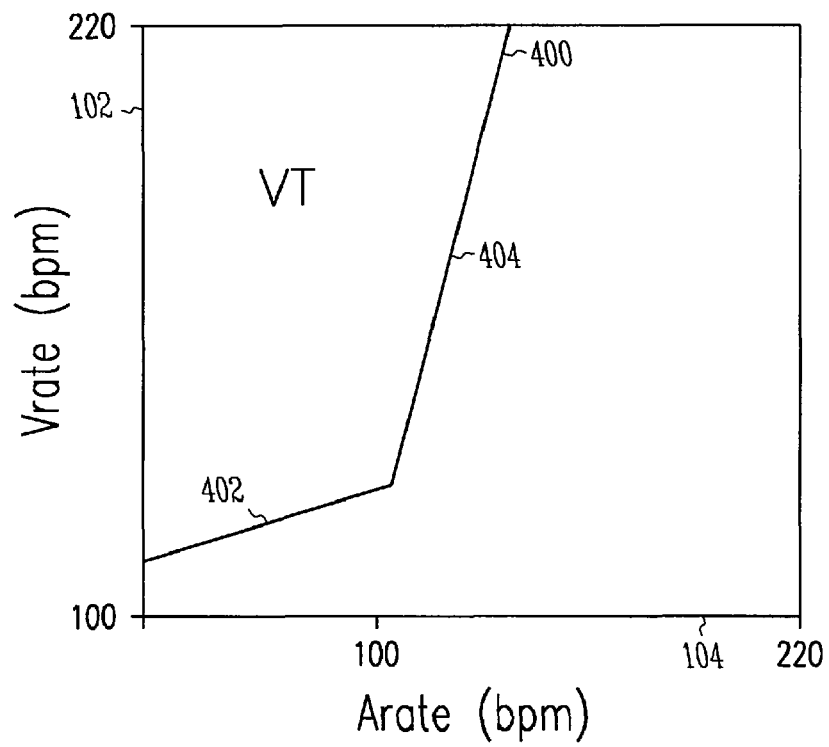
FIG. 4 is a graph that illustrates an alternative example in which a bilinear threshold boundary includes a line segment that has a slope that is less than 0.5, and line segment that has a slope that is greater than 0.5.

In the example of FIG. 3, the breakpoint 306 is located at about VR=180 bpm and AR=170 bpm, however, FIG. 3 is merely exemplary and is drawn to emphasize the conceptual nature of the rate dependent threshold as represented by a threshold boundary. The exact location of the breakpoint 306 or the slope of line segment 302 is typically determined using data (such as shown in FIG. 1) along with a desired specificity of classifying the arrhythmia as a VT. Moreover, the line segment 304 need not be rate independent (e.g., slope=0.5), but may also be rate dependent. FIG. 4 is a graph that illustrates an alternative example in which a bilinear threshold boundary 400 includes a line segment 402 that has a slope that is less than 0.5, and line segment 404 that has a slope that is greater than 0.5.

Figure 5:
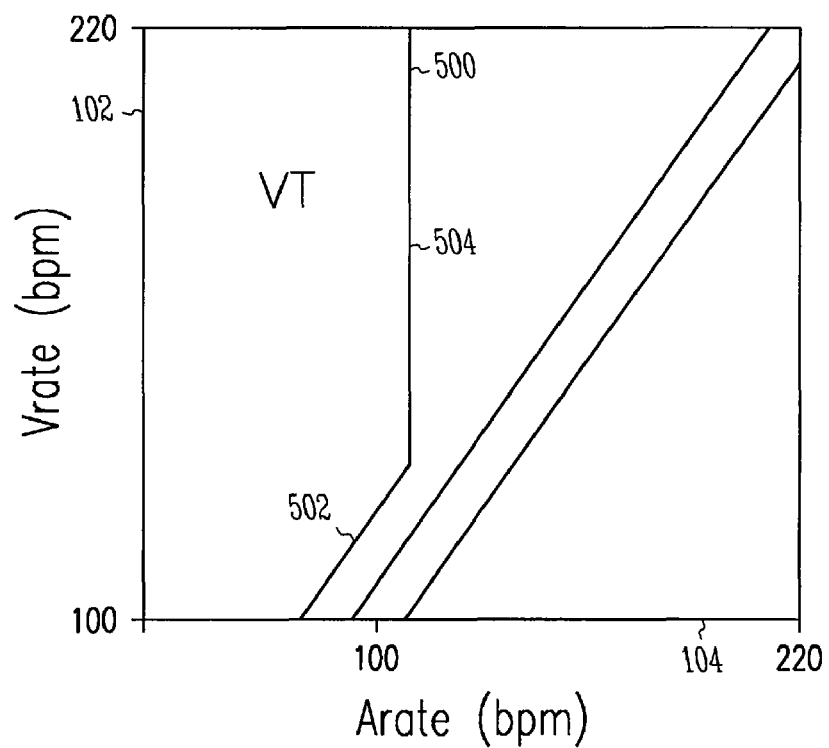
FIG. 5 is a graph illustrating an alternative example of a bilinear threshold boundary comprising a lower rate line segment, and a higher rate line segment that has substantially infinite slope, such as to implement an atrial rate cutoff value.

FIG. 5 is a graph illustrating an alternative example of a bilinear threshold boundary 500 comprising a lower rate line segment 502 and a higher rate line segment 504. In this example, the higher rate line segment 504 has substantially infinite slope, as illustrated in FIG. 5. This effectively implements an atrial rate cutoff value, such as by extrapolating the line segment 504 to the corresponding atrial rate on the x-axis 104. In this example, an arrhythmia occurring at an observed AR greater than the atrial rate cutoff value (e.g., about 110 bpm, in the example illustrated in FIG. 4) will not be classified as a VT, regardless of the VR value observed during that arrhythmia. Although the line segment 502 is shown in FIG. 5 as being rate independent (i.e., slope=0.5), it could also be made rate dependent (for example, slope less than 0.5).

Figure 6:
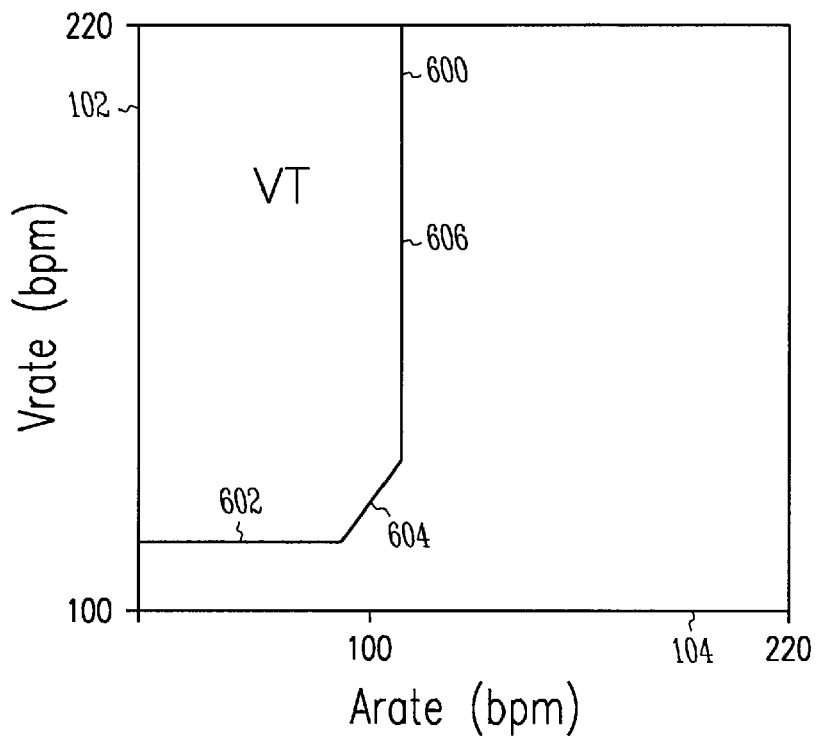
FIG. 6 is a graph illustrating an alternative example in which the rate-dependent threshold boundary is piecewise linear, such as by including more than two line segments.

FIG. 6 is a graph illustrating an alternative example in which the rate-dependent threshold boundary 600 is piecewise linear, such as by including more than two line segments. In the example of FIG. 6, the rate dependent threshold boundary 600 includes three line segments 602, 604, and 606, having slopes of 0, 0.5, and ∞, respectively, although other slopes or breakpoints are also contemplated.

Figure 7:
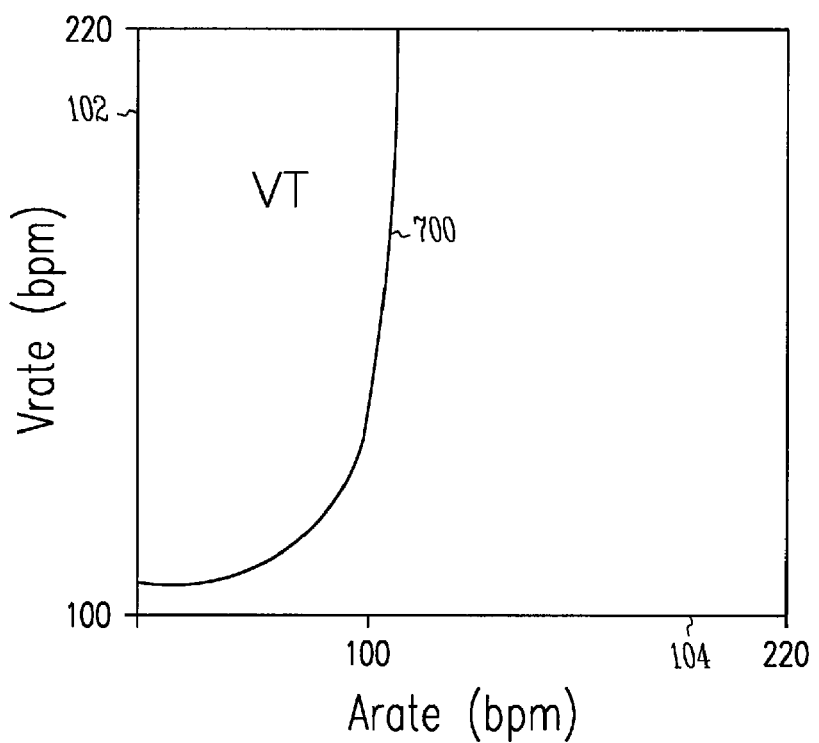
FIG. 7 is a graph illustrating an alternative example in which the rate dependent threshold boundary is curvilinear.

FIG. 7 is a graph illustrating an alternative example in which the rate dependent threshold boundary 700 is not piecewise linear, but is instead curvilinear.

Figure 8:
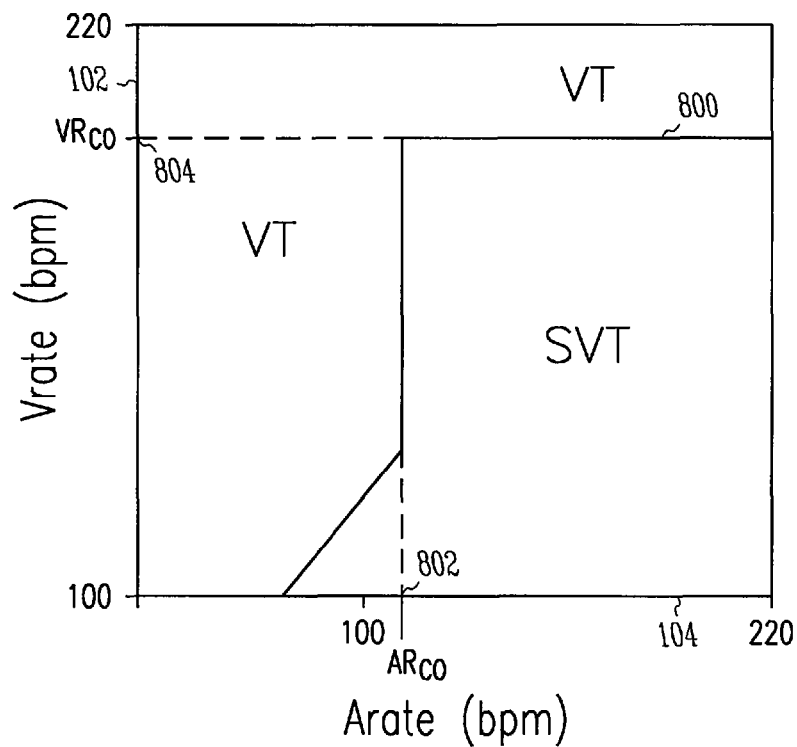
FIG. 8 is a graph illustrating an alternative example in which the rate dependent threshold boundary implements both an atrial rate cutoff and a ventricular rate cutoff.

FIG. 8 is a graph illustrating an alternative example in which the rate dependent threshold boundary 800 implements both an atrial rate cutoff ($AR_{co}$) 802 and a ventricular rate cutoff ($VR_{co}$) 804. In this example, the ventricular rate cutoff has priority over the atrial rate cutoff. That is, if the tachyarrhythmia is observed at a VR that exceeds the ventricular rate cutoff 804, then the tachyarrhythmia is classified as a VT regardless of the AR. Otherwise, if tachyarrhythmia is observed at an AR that exceeds the atrial rate cutoff 802, the tachyarrhythmia is classified as an SVT regardless of the VR. Otherwise, the tachyarrhythmia is classified as a VT if the VR exceeds the AR by the threshold value (i.e., by the distance between the threshold boundary and the AR=VR line).

Although the above examples have been discussed with respect to classifying a tacharrhythmia as a VT, similar examples also apply to classifying a tachyarrhythmia as SVT. In one example, the above described techniques may classify as an SVT any tacharrhythmia that is not deemed a VT. In another example, however, the SVT classification uses a separate test. That separate test may be individually tailored to classify the SVT with greater specificity than would be the case if a single test were used to classify a detected arrhythmia as a VT or an SVT.

Figure 9:
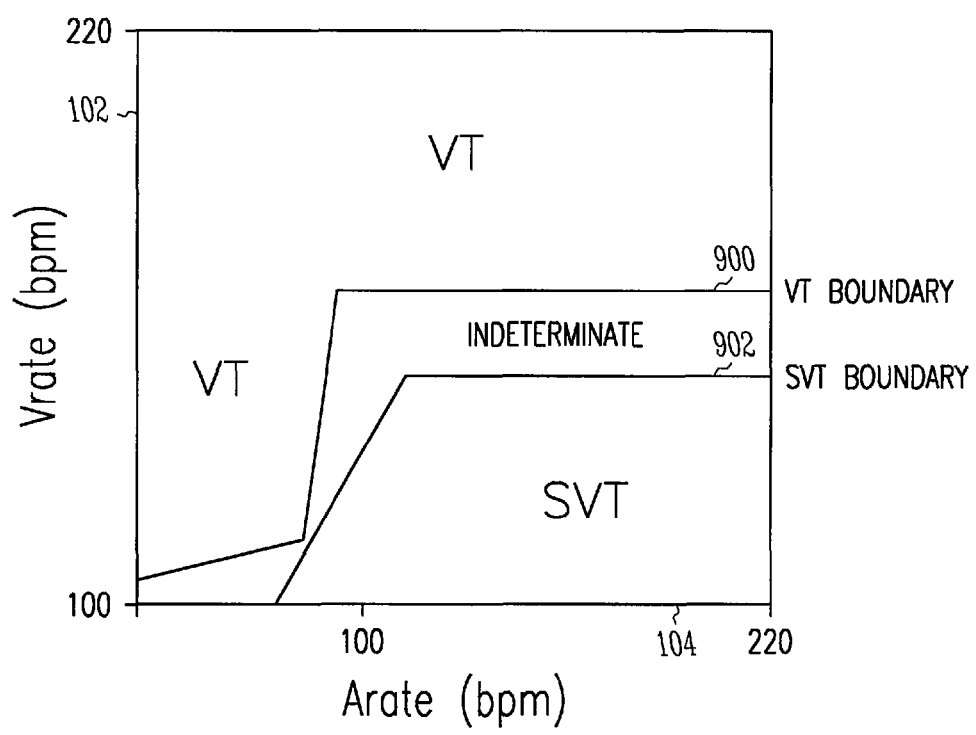
FIG. 9 is a graph illustrating an example of a rate dependent VT threshold boundary that is separate or different from the rate dependent SVT threshold boundary.

FIG. 9 is a graph illustrating an example of a rate dependent VT threshold boundary 900 that is separate or different from the rate dependent SVT threshold boundary 902. Because using separate boundaries may result in one or more indeterminate regions (either because the tachyarrhythmia is not classified as either a VT or an SVT, or because the tachyarrhythmia is classified as both a VT or SVT), it may be desirable to use the rate dependent threshold techniques described in this document together with one or more other VT/SVT discrimination techniques. Examples of other VT/SVT discrimination techniques include, by way of example, but not by way of limitation, stability, onset, vector timing, or correlation. The particular classification may be made by weighting or otherwise combining the results of more than one discrimination technique, either for the case of separate VT and SVT threshold boundaries as shown in FIG. 9, or for the other examples such as illustrated in FIGS. 1-8. Moreover, the examples shown in FIGS. 1-9 or elsewhere in this document can be used in combination with each other, or in combination with other VT/SVT discrimination techniques.

Figure 10:
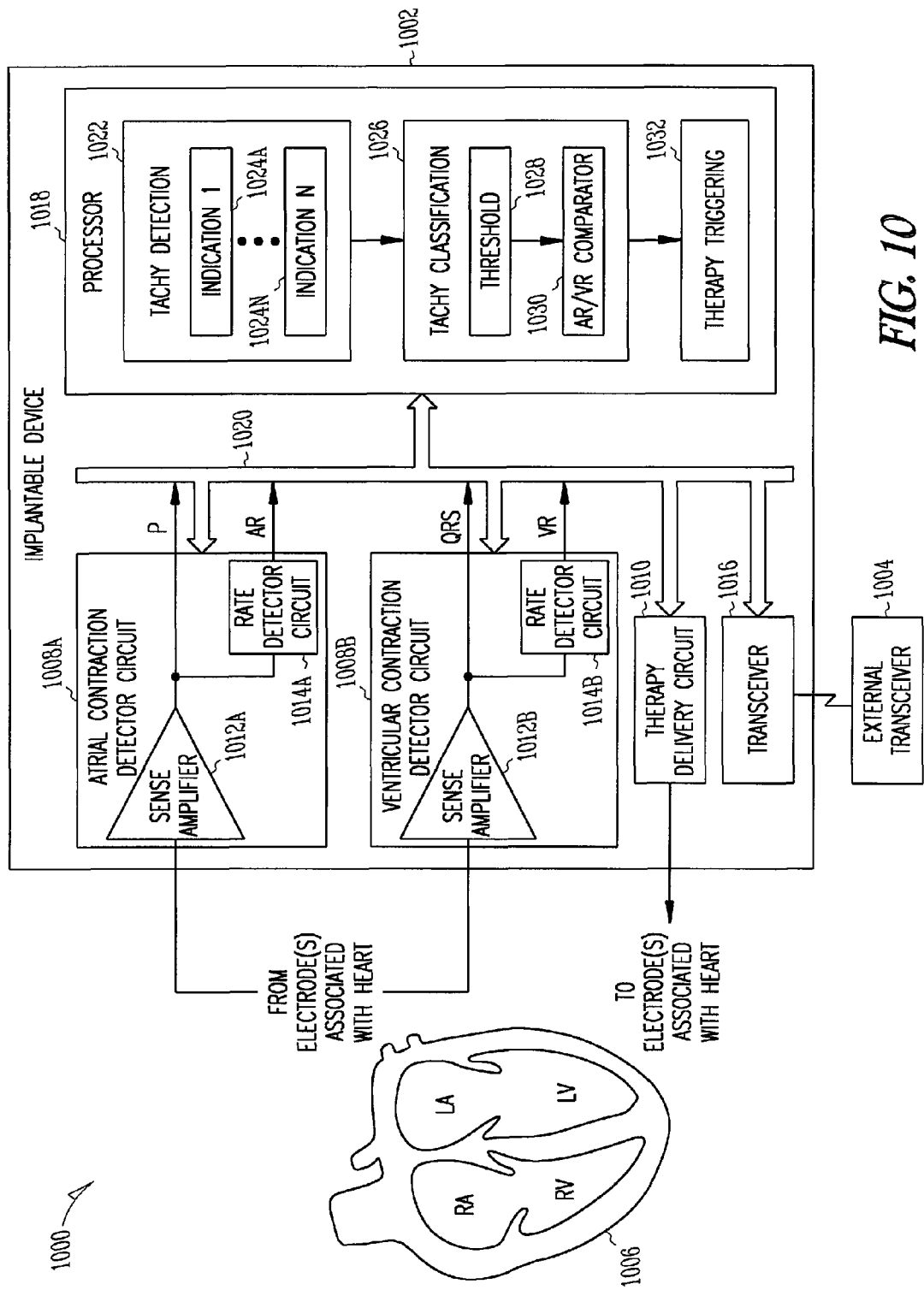
FIG. 10 is a block diagram illustrating generally one example of a system providing VT/SVT discrimination.

FIG. 10 is a block diagram illustrating generally one example of a system 1000 providing the VT/SVT discrimination techniques described above. In FIG. 10, the system 1000 includes a cardiac rhythm management (CRM) or other implantable device 1002, which may be accompanied by an external transceiver 1004 of an external programmer, a repeater, or other communication device. The implantable device 1002 is coupled to a patient's heart 1006, such as by one or more intravascular or other leads carrying electrodes or the like for sensing heart signals or providing anti-tachyarrhythmia or other therapy to the heart 1006.

In the example of FIG. 10, the implantable device 1002 includes an atrial heart contraction detector circuit 1008A and a ventricular heart contraction detector circuit 1008B. The heart contraction detector circuits 1008A-B detect heart contractions associated with a respective atrium or ventricle of the heart 1006, such as by sensing the intrinsic electrical heart signals from the heart chamber or by detecting triggering signals from contraction-evoking pulses delivered by a therapy circuit 1010 to the heart chamber.

The atrial contraction detector circuit 1008A includes a sense amplifier 1012A providing an output signal representative of the intrinsic atrial heart signal. This output signal includes electrical depolarizations (called "P-waves") representing successive atrial heart contractions. The output signal is received by an atrial rate detector circuit 1014A, which measures a time between successive atrial heart contractions to provide an output indication of the atrial rate ("AR").

Similarly, the ventricular contraction detector circuit 1008B includes a sense amplifier 1012B providing an output signal representative of the intrinsic ventricular heart signal. This output signal includes electrical depolarizations (called "QRS-complexes") representing successive ventricular heart contractions. The output signal is received by a ventricular rate detector circuit 1014B, which measures a time between successive ventricular heart contractions to provide an output indication of the ventricular rate ("VR").

The therapy delivery circuit 1010 typically includes one or more of: a pace pulse delivery circuit, an anti-tachyarrhythmia therapy circuit, a cardiac resynchronization therapy circuit, a cardiac contractility modulation (CCM) circuit, or any other therapy delivery circuit. The anti-tachyarrhythmia therapy circuit typically includes at least one defibrillation circuit or anti-tachyarrhythmia pacing (ATP) circuit or the like.

In the example of FIG. 10, the implantable device 1002 also includes a transceiver 1016 for wirelessly communicating with the external transceiver 1004. The implantable device 1002 also includes a processor 1018. The processor 1018 is coupled to the other circuits of the implantable device 1002 by at least one bus 1020 or the like. The processor 1018 is implemented as any controller or other circuit that is capable of sequencing through various control states such as, for example, by using a digital microprocessor having executable instructions stored in an associated instruction memory circuit, a microsequencer, or a state machine.

In the example of FIG. 10, the processor 1018 includes a tachyarrhythmia detection circuit 1022. The tachyarrhythmia detection circuit 1022 processes signals received from the atrial contraction detector circuit 1008A or the ventricular contraction detector circuit 1008B. In response, the tachyarrhythmia detection circuit 1022 provides one or more indications 1024A-N that a tachyarrhythmia is present. As one illustrative example, an a first indication 1024A (sometimes referred to as an "Onset" indication) deems three consecutive "fast" (for example, at a rate greater than about 165 bpm) intervals between contractions of the same heart chamber as providing a first indication 1024 of an onset of a tachyarrhythmia.

In this same example, if the first indication 1024A indicates an onset of a tachyarrhythmia, then this triggers a second test for a second indication 1024N (sometimes referred to as a "Duration" indication). This second test looks for the presence of three of ten fast intervals occurring during a time period referred to as the "duration" period. If this condition is met, then the second indication 1024N of a tachyarrhythmia is also present. In this way, a desired number of tachyarrhythmia indications can be used conjunctively to increase the specificity of a tachyarrhythmia detection before anti-tachyarrhythmia therapy is delivered.

The example of FIG. 10 also includes a tachyarrhythmia classification circuit 1026. In one example, the tachyarrhythmia classification circuit 1026 performs the VT/SVT discrimination, such as discussed above. Therefore, in one example, the tachyarrhythmia classification circuit 1026 includes a rate-dependent threshold 1028 (such as discussed above). The rate-dependent threshold 1028 is provided to a comparator 1030 that compares atrial and ventricular rates, using the rate-dependent threshold, to classify the tachyarrhythmia as VT or SVT. The rate-dependent threshold 1028 can be stored in one or more memory locations in various different forms, such as an equation, a lookup table, or in any other desired form.

The comparator 1030 compares the atrial rate and the ventricular rate using the rate-dependent threshold 1028. In one example of classifying a tachyarrhythmia as VT, the tachyarrhythmia classification circuit uses a ventricular rate (or atrial rate) received from the ventricular rate detector circuit 1014B (or the atrial rate detector 1014A) as an index into a rate-dependent function that yields a threshold value for comparing AR and VR. If VR exceeds AR by at least the threshold value, then the tachyarrhythmia classification circuit deems the tachyarrhythmia to be a VT instead of an SVT.

In the example of FIG. 10, the processor 1018 also includes a therapy triggering circuit 1032 that triggers an appropriate anti-tachyarrhythmia therapy in response to the tachyarrhythmia detection indication(s) from the tachyarrhythmia detection circuit 1022 and the tachyarrhythmia classification from the tachyarrhythmia classification circuit 1026. As an illustrative example, a detected tachyarrhythmia that is classified as VT may be treated with a defibrillation shock, while a detected tachyarrhythmia that is classified as an SVT may be treated by an anti-tachyarrhythmia pacing (ATP) pulse sequence. In general, there may be many different therapy responses, with the particular therapy response depending on the tachyarrhythmia classification or the particular tachyarrhythmia detection indication(s) that are present.

Figure 11:
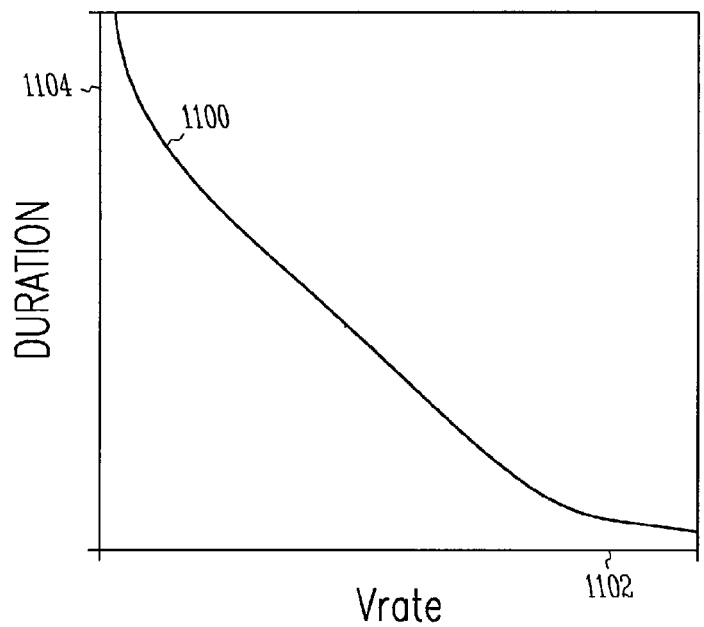
FIG. 11 is a graph of a duration interval function, in which the y-axis represents the value of the duration interval and the x-axis represents a ventricular rate.

In one example, at least one of the tachyarrhythmia detection indications 1024A-N is rate-dependent. In one example, the "duration" time interval discussed above is also rate dependent, as illustrated conceptually in FIG. 11. FIG. 11 is a graph of a duration interval function 1100, in which the y-axis 1102 represents the value of the duration interval and the x-axis 1104 represents a ventricular rate. In this example, the duration interval function 1100 automatically substantially continuously decreases monotonically with increasing ventricular rate. In the example illustrated in FIG. 11, a test for "X" of "Y" fast intervals is carried out over a shorter duration interval period at a higher ventricular rate than for a lower ventricular rate. The actual numbers for "X" and "Y" may also typically vary as a function of the ventricular rate. The example discussed earlier tested for X=6 of Y=10 fast intervals occurring during a duration period (e.g., 2.5 seconds). In one rate-dependent duration interval period example, this duration period corresponds to a VR=160 bpm. As one illustrative example, at a lower VR=130, a duration period of about 5 seconds is used, and the corresponding tachyarrhythmia detection test looks for X=12 of Y=20 fast R-R intervals between successive ventricular contractions. Continuing with this illustrative example, at a higher VR=240, a duration period of about 1 second is used, and the corresponding tachyarrhythmia detection test looks for X=3 of Y=5 fast R-R intervals. These values are provided for illustrative purposes only, the exact values may be programmed as desired. In one example, such programming is performed by the manufacturer, so that the physician need not program various durations corresponding to various ventricular rates. Such automaticity increases the ease of use of the implantable device 1002.

Figure 12:
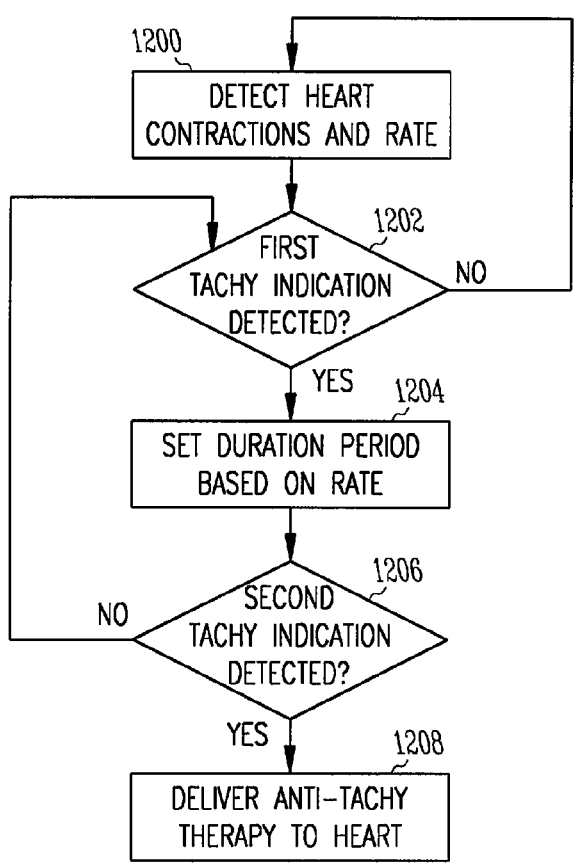
FIG. 12 is a flow chart illustrating generally one example of using at least one rate-dependent tachyarrhythmia detection criterion.

FIG. 12 is a flow chart illustrating generally one example of using at least one rate-dependent tachyarrhythmia detection criterion. In the example of FIG. 12, at 1200, heart contractions and heart rate are detected. In one example this includes detecting ventricular heart contractions and ventricular heart rate. At 1202, a first test is performed to determine if a tachyarrhythmia is present. In one illustrative example, if three consecutive fast intervals between successive ventricular contractions is detected, an "onset" of a tachyarrhythmia is deemed present, and process flow continues at 1204; otherwise process flow returns to 1200. At 1204, a "duration period" parameter of a second tachyarrhythmia detection test corresponding to a particular heart rate is established. In one example, a substantially continuously decreasing duration vs. ventricular rate function, as illustrated in FIG. 11, is used to automatically set the duration period at 1204. At 1206, a second test is performed to confirm that the tachyarrhythmia is present. In one illustrative example, if three of ten fast intervals (intervals shorter than a threshold interval value) between successive ventricular contractions are detected during the duration period that was selected using the ventricular rate, then the tachyarrhythmia is deemed to be present. In a further example, the second test determines if X of Y fast intervals is present during the automatically selected duration period, where X or Y is also selected using the rate. If the second test deems a tachyarrhythmia to be present, then process flow continues to 1208, and anti-tachyarrhythmia therapy is delivered to the heart.

In the above example, the rate-dependent duration period can alternatively be used as a single tachyarrhythmia detection test (e.g., without a first tachyarrhythmia detection criterion, such as the onset), or could be used in conjunction with one or more additional tachyarrhythmia detection criteria. Also, the above example could also be used in conjunction with a tachyarrhythmia classification before anti-tachyarrhythmia therapy is delivered. This permits the particular anti-tachyarrhythmia therapy to be tailored using the classification or the tachyarrhythmia detection indication(s). The rate-dependent duration period can be used with a rate-dependent threshold for arrhythmia detection, as discussed above, or with a rate-independent threshold for arrhythmia detection, if desired.

Figure 13:
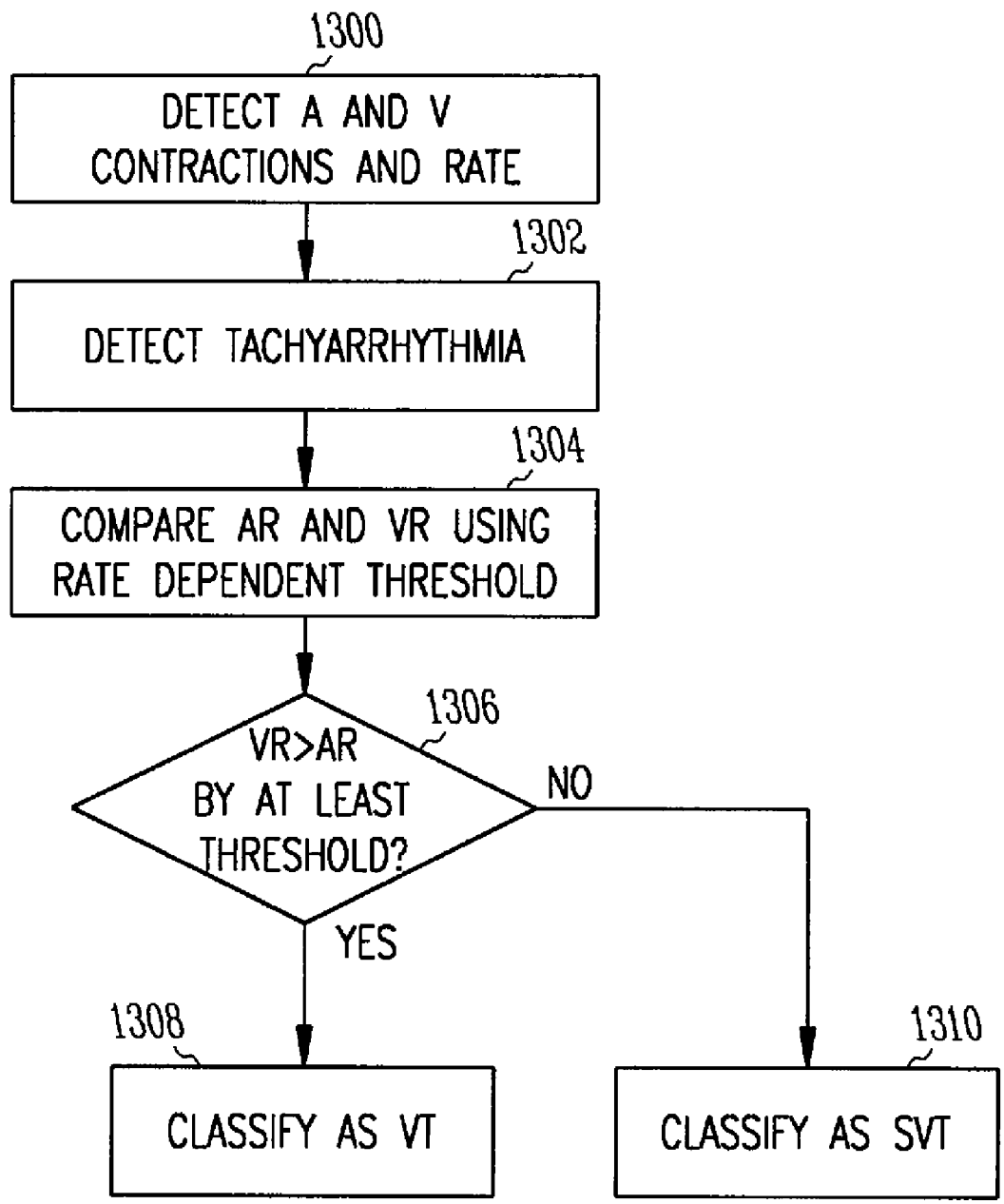
FIG. 13 is a flow chart illustrating generally one example of tachyarrhythmia classification.

FIG. 13 is a flow chart illustrating generally one example of tachyarrhythmia classification. In the example of FIG. 13, at 1300, atrial and ventricular contractions and rate are detected. At 1300, atrial and ventricular contractions and corresponding rates are detected. At 1302, a tachyarrhythmia is detected, such as by using one or more tachyarrhythmia detection criteria (e.g., onset test, duration test, etc.), examples of which are discussed above. At 1304, atrial rate and ventricular rate are compared using a bilinear, piecewise linear, curvilinear or other rate-dependent threshold, as discussed above. The particular threshold value used for the comparison is selected using one of ventricular rate or atrial rate. At 1306, if VR exceeds AR by the threshold value corresponding to the observed heart rate, then at 1308, the tachyarrhythmia is classified as a VT. Otherwise, at 1310, the tachyarrhythmia is either classified as an SVT, or a separate SVT classification routine is initiated at 1310. In one example, after the classification is made, an anti-tachyarrhythmia therapy is then delivered. In another example, after the classification is made, one or more classification-specific tachyarrhythmia detection criteria is then applied to further enhance the specificity of the detection. In yet a further example, the anti-tachyarrhythmia therapy is tailored using one of the classification or the tachyarrhythmia detection criteria.

Figure 14:
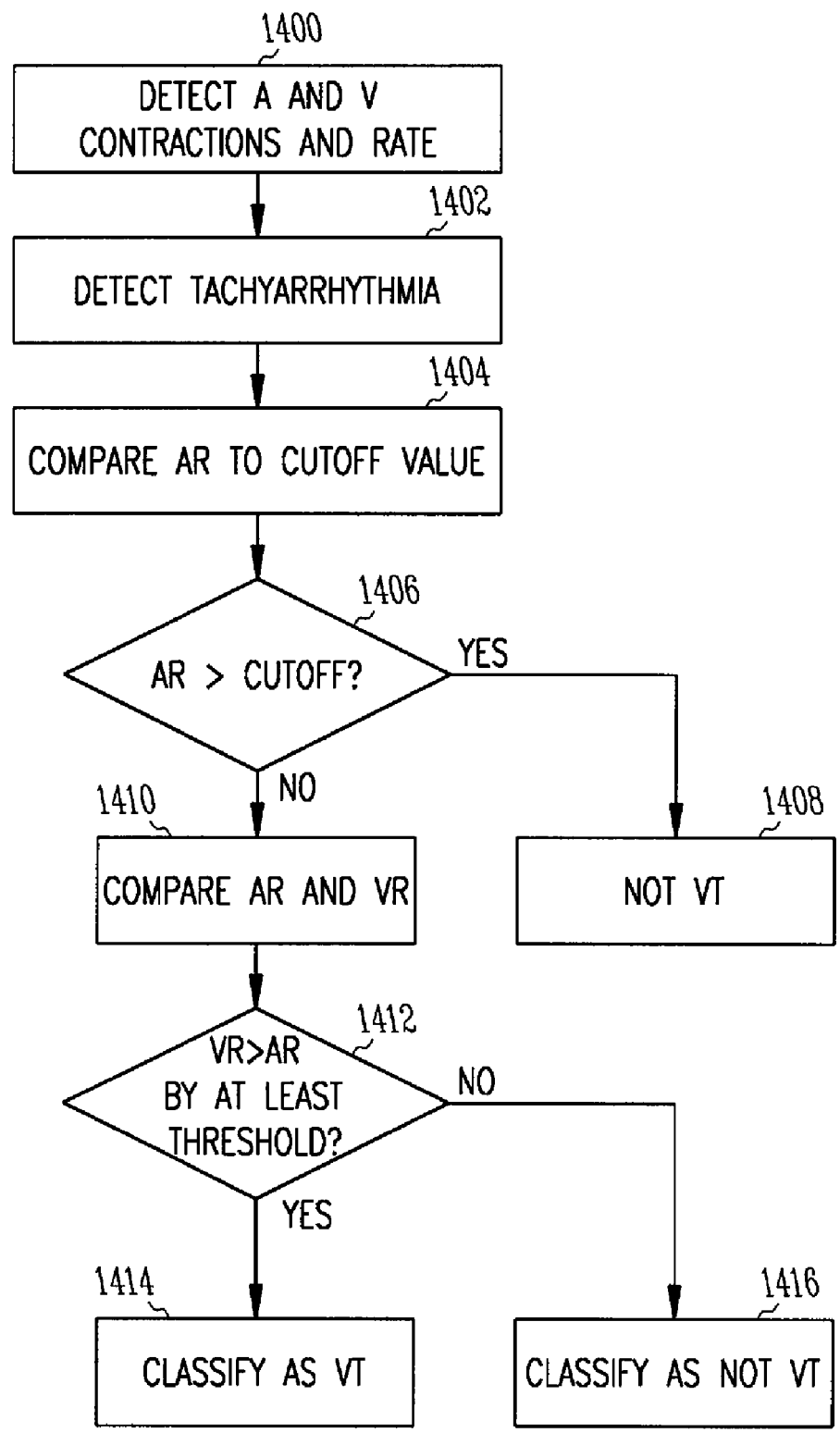
FIG. 14 is a flow chart illustrating generally one example of a technique of classifying a tachyarrhythmia using a rate cutoff value.

FIG. 14 is a flow chart illustrating generally one example of a technique of classifying a tachyarrhythmia using a rate cutoff value. In the example of FIG. 14, at 1400, atrial and ventricular contractions and rates are detected. At 1402, a tachyarrhythmia is detected using one or more tachyarrhythmia detection indications. In one example, at least one of these tachyarrhythmia detection indications uses a rate-dependent duration period, as discussed above. At 1404, the atrial rate is compared to a cutoff value. At 1406, if the atrial rate exceeds the cutoff value, then, at 1408, the detected arrhythmia is deemed not a VT. Otherwise, at 1410, atrial rate and ventricular rates are compared. In one example, this comparison includes using a bilinear, piecewise linear, curvilinear, or other rate-dependent threshold value. In another example, this comparison includes using a rate-independent threshold value. At 1412, if the ventricular rate exceeds the atrial rate by at least the threshold value, then, at 1414, the tachyarrhythmia is classified as a VT. Otherwise, at 1416, the tachyarrhythmia is classified as not VT. In one example, after the classification is made, an anti-tachyarrhythmia therapy is then delivered. In another example, after the classification is made, one or more classification-specific tachyarrhythmia detection criteria is then applied to further enhance the specificity of the detection. In yet a further example, the anti-tachyarrhythmia therapy is tailored using one of the classification or the tachyarrhythmia detection criteria.

Alternatively, the example illustrated in FIG. 14 is used to implement a ventricular rate cutoff instead of an atrial rate cutoff, in which a ventricular rate exceeding the corresponding ventricular rate cutoff results in the detected tachyarrhythmia being classified as a VT.

Figure 15:
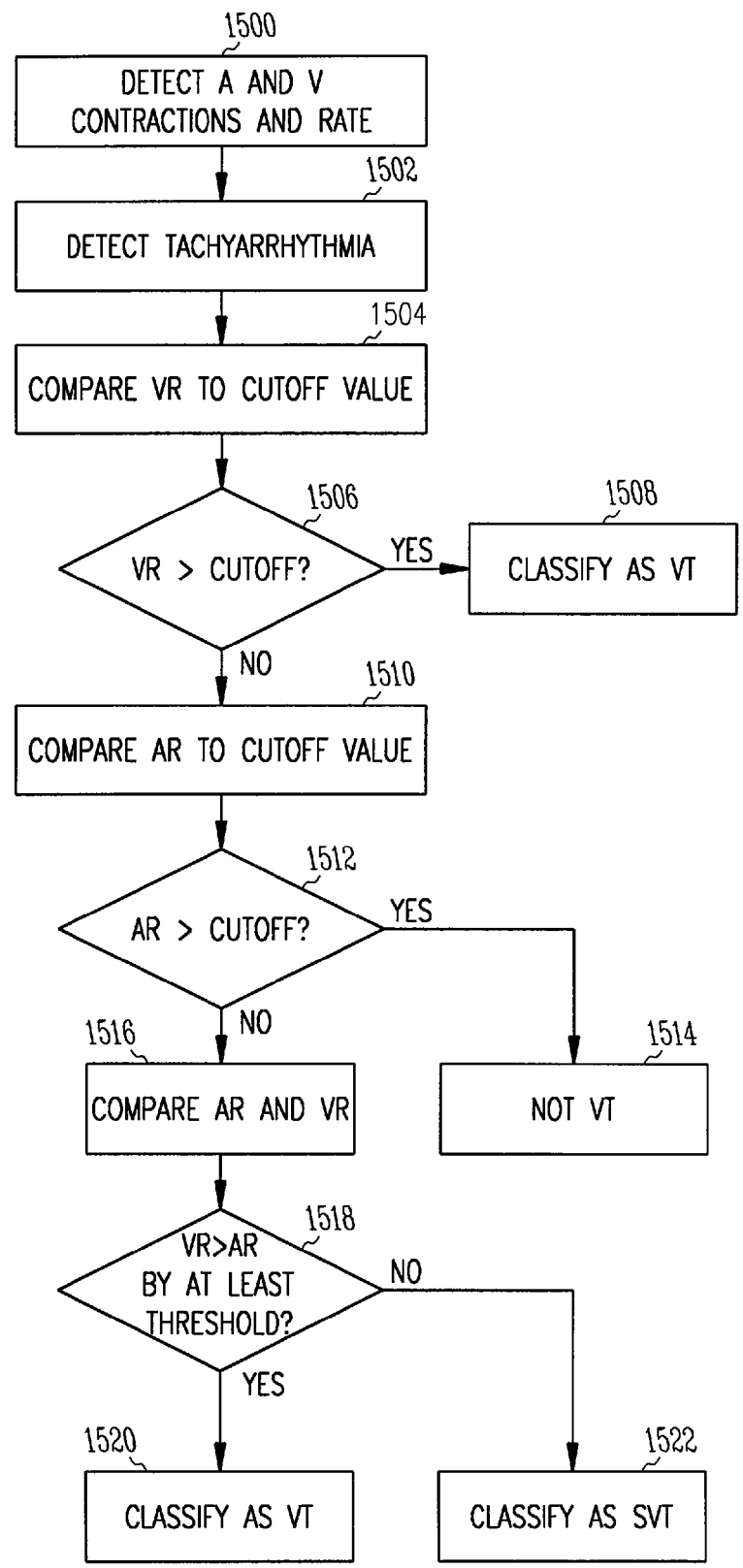
FIG. 15 is a flow chart illustrating generally an example of a technique of classifying a tachyarrhythmia using ventricular and atrial rate cutoff values.

FIG. 15 is a flow chart illustrating generally an example of a technique of classifying a tachyarrhythmia using ventricular and atrial rate cutoff values. In the example of FIG. 15, at 1500, atrial and ventricular contractions and rates are detected. At 1502, a tachyarrhythmia is detected using one or more tachyarrhythmia detection indications. In one example, at least one such tachyarrhythmia detection indication uses a rate-dependent duration period, as discussed above. At 1504, the ventricular rate is compared to a cutoff value. At 1506, if the ventricular rate exceeds the cutoff value, then, at 1508, the detected arrhythmia is deemed a VT. Otherwise, at 1510, the atrial rate is compared to a cutoff value. At 1512, if the ventricular rate exceeds the cutoff value, then, at 1514, the detected arrhythmia is deemed not a VT. Otherwise, at 1516, atrial rate and ventricular rates are compared. In one example, this comparison includes using a bilinear, piecewise linear, curvilinear, or other rate-dependent threshold value, as discussed above. In another example, this comparison includes using a rate-independent threshold value. At 1518, if the ventricular rate exceeds the atrial rate by at least the threshold value, then, at 1520, the tachyarrhythmia is classified as a VT. Otherwise, at 1522, the tachyarrhythmia is classified as not VT. In one example, after the classification is made, an anti-tachyarrhythmia therapy is then delivered. In another example, after the classification is made, one or more classification-specific tachyarrhythmia detection criteria is then applied to further enhance the specificity of the detection. In yet a further example, the anti-tachyarrhythmia therapy is tailored using one of the classification or the tachyarrhythmia detection criteria.

OTHER EXAMPLES

In other examples, the concept of rate-dependent thresholds can be applied to other rhythm discrimination parameters, such as stability, onset, or morphology correlation.

Figure 16:
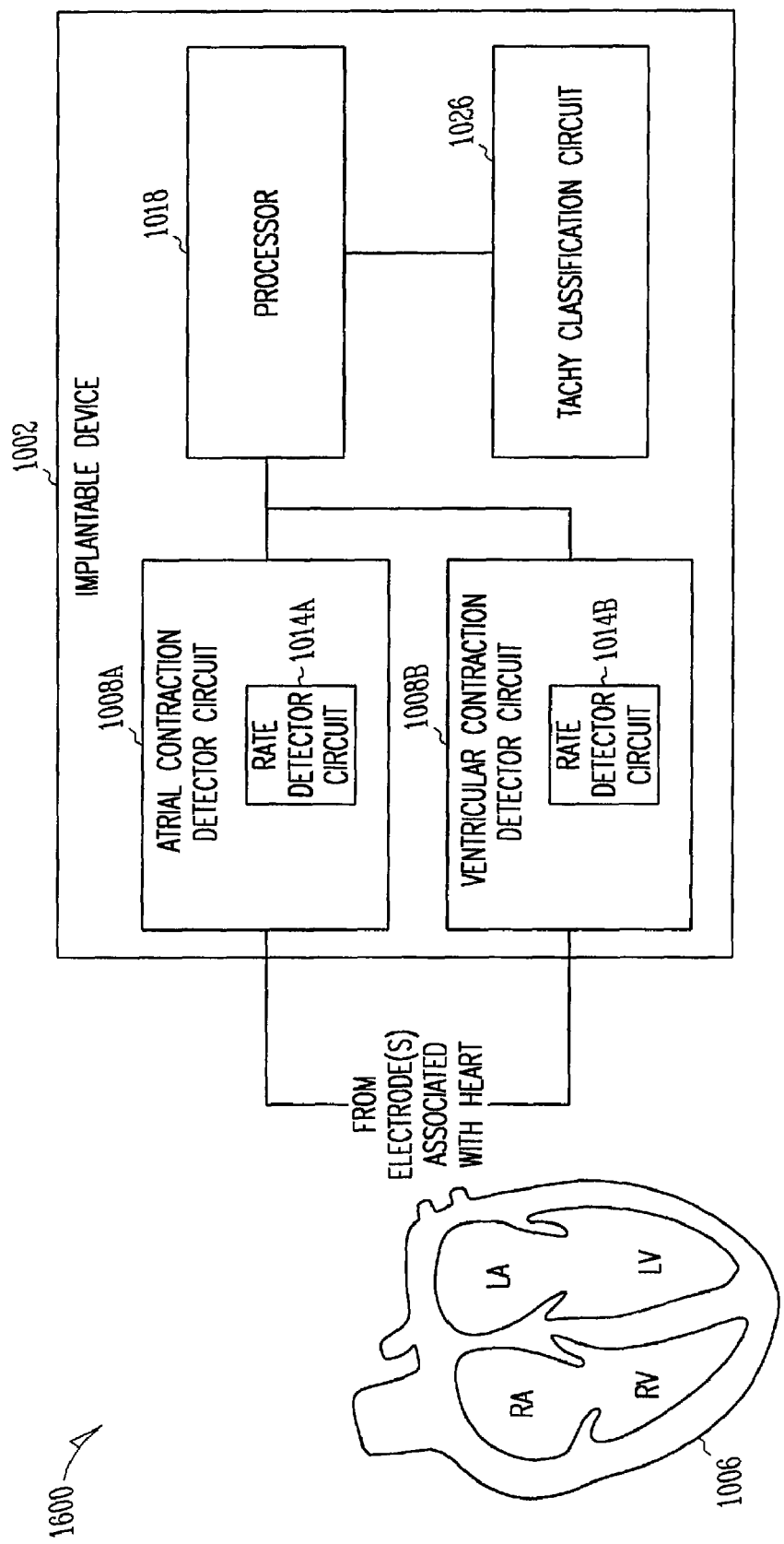
FIG. 16 is a block diagram illustrating generally an example of a system including a tachyarrhythmia classification circuit.

FIG. 16 illustrates generally an example of a system 1600 including a cardiac rhythm management (CRM) or other implantable device 1002 that can be coupled to a subject's heart 1006, such as by one or more intravascular or other leads carrying electrodes or the like for sensing heart signals or providing anti-tachyarrhythmia or other therapy to the heart 1006. The system 1600 can include an atrial contraction detector circuit 1008A, a ventricular contraction detector circuit 1008B, a processor 1018, and a tachyarrhythmia classification circuit 1026. In FIG. 16, the atrial contraction detector circuit 1008A can include an atrial rate detector circuit 1014A, and the ventricular contraction detector circuit 1008B can include a ventricular rate detector circuit 1014B. In this example, the atrial contraction detector circuit 1008A, the ventricular contraction detector circuit 1008B, and the tachyarrhythmia classification circuit 1026 are coupled to the processor 1018. In other examples, at least a portion of one or more of the processor 1018 or the tachyarrhythmia classification circuit 1026 can be configured to be located external to the implantable device 1002 or external to or even remote from the subject. In certain examples, at least some of the functionality of the tachyarrhythmia classification circuit 1026 can be implemented using the processor 1018, or the processor 1018 can include the tachyarrhythmia classification circuit 1026.

The atrial contraction detector circuit 1008A can be configured to detect an atrial contraction of the heart 1006 and the atrial rate detector circuit 1014A can be configured to detect an atrial rate between atrial contractions of the heart 1006. In an example, the atrial rate detector circuit 1014A can be configured to detect an atrial interval between atrial contractions of the heart 1006. The atrial rate detector circuit 1014A can be configured to detect the atrial rate using the detected atrial interval. In an example, the atrial rate detector circuit 1014A can be configured to represent the atrial rate using the atrial interval.

The ventricular contraction detector circuit 1008B can be configured to detect a ventricular contraction of the heart 1006, and the ventricular rate detector circuit 1014B can be configured to detect a ventricular rate between ventricular contractions of the heart 1006. In an example, the ventricular rate detector circuit 1014B can be configured to detect a ventricular interval between ventricular contractions of the heart 1006. The ventricular rate detector circuit 1014B can be configured to detect the ventricular rate using the detected ventricular interval. In an example, the ventricular rate detector circuit 1014B can be configured to represent the ventricular rate using the ventricular interval.

The tachyarrhythmia classification circuit 1026 can be configured to classify a tachyarrhythmia using a rhythm discrimination parameter having a value. In certain examples, the rhythm discrimination parameter can include stability, onset, or morphology correlation.

In an example, the rhythm discrimination parameter can include stability, such as that disclosed in the commonly assigned Gilkerson et al. U.S. Pat. No. 6,493,579 entitled "SYSTEM AND METHOD FOR DETECTION ENHANCEMENT PROGRAMMING," (herein "Gilkerson et al. '579") which is hereby incorporated by reference in its entirety, including its disclosure of using stability to detect clinical rhythms. Generally, the rhythm discrimination parameter stability is configured to detect an unstable cardiac rhythm. The unstable cardiac rhythm, such as an unstable ventricular rate or interval, can be indicative of atrial fibrillation that is conducted to the ventricle. In certain examples, an unstable cardiac rhythm can be detected by analyzing the shortest or longest intervals in a plurality of atrial or ventricular contractions, by analyzing the standard deviation or other variability of the intervals in the plurality of contractions, or by analyzing the number of intervals that fall outside of a variability range such as can be defined by a specified number of the standard deviations of the intervals in the plurality of contractions. In an example, the value of rhythm discrimination parameter stability can include a variance threshold or other threshold measurement or indicator of an unstable rhythm to which a particular rhythm can be compared.

In another example, the rhythm discrimination parameter can include onset, such as that disclosed in Gilkerson et al. '579, which is incorporated by reference in its entirety, including its disclosure of using onset to detect clinical rhythms. Generally, the rhythm discrimination parameter onset is configured to detect a sudden change in cardiac rhythm. The sudden change in cardiac rhythm, such as a sudden increase in the ventricular rate or a sudden decrease in the ventricular interval, can be indicative of a ventricular tachyarrhythmia. In certain examples, a sudden change in the cardiac rhythm can be detected by monitoring the intervals between atrial or ventricular contractions and comparing an interval to a subsequent or previous interval, or a subsequent or previous average or other central tendency of multiple intervals. In an example, the value of the rhythm discrimination parameter onset can include a rate progression threshold or other threshold measurement or indicator of a sudden change in cardiac rhythm.

In another example, the rhythm discrimination parameter can include morphology correlation, such as that disclosed in the commonly assigned Li U.S. patent application Ser. No. 11/151,567 entitled "METHOD AND APPARATUS FOR RATE-DEPENDENT MORPHOLOGY-BASED CARDIAC ARRHYTHMIA," (herein "Li '567") which is hereby incorporated by reference in its entirety, including its disclosure of using a correlation between the morphological features of a template and candidate arrhythmic waveforms to classify an arrhythmia. Generally, the rhythm discrimination parameter morphology correlation is configured to detect the similarity between a candidate waveform, such as the ventricular contraction, and a template (e.g., the detected similarity between the candidate waveform and the template can include a morphology correlation value). The correlation is generally the degree to which the candidate waveform and the template are similar. In certain examples, the template can include a normal sinus rhythm template, such as a normal sinus rhythm ventricular contraction template, or the template can include a tachyarrhythmia template, such as a tachyarrhythmia ventricular contraction template. The template can include clinical information, such as population information from subjects with similar cardiac conditions, or the template can include subject-specific information, such as previously acquired waveforms from the subject. In an example, the value of the rhythm discrimination parameter morphology correlation can include a morphology correlation threshold or other threshold that can be applied to the similarity between the waveform and the template.

In other examples, the rhythm discrimination parameter can include other rhythm discrimination parameters, such as the ventricular rate exceeding the atrial rate V Rate>A Rate), an atrial fibrillation rate (AFib Rate), or a sustained rate duration, each having other values, such as a ventricular rate threshold, an atrial rate threshold, or a sustained rate threshold.

In the example of FIG. 16, the processor 1018 can be configured to adjust the value of the rhythm discrimination parameter such as by using a relationship between the atrial rate and the ventricular rate. In certain examples, the relationship between the atrial rate and the ventricular rate can include information about the amount that the ventricular rate exceeds the atrial rate, or the relationship between the atrial rate and the ventricular rate can include information about the amount that the atrial rate exceeds the ventricular rate. In an example, the information about the amount that the ventricular rate exceeds the atrial rate, or the atrial rate exceeds the ventricular rate, can include the amount by which the ventricular rate exceeds the atrial rate, or the atrial rate exceeds the ventricular rate, by at least a threshold.

In another example, the processor 1018 can be configured to adjust the value of the rhythm discrimination parameter such as by using at least one of the atrial rate or the ventricular rate (e.g., using the atrial rate, using the ventricular rate, or using the atrial rate and the ventricular rate) in addition to using the relationship between the atrial rate and the ventricular rate. For example, this can include using the amount by which the ventricular rate exceeds the atrial rate as a function of at the atrial rate, using the amount by which the ventricular rate exceeds the atrial rate as a function of the ventricular rate, or using the amount by which the ventricular rate exceeds the atrial rate as a function of the atrial rate and the ventricular rate.

In other examples, the processor 1018 can be configured to adjust the value of the rhythm discrimination parameter using information about whether (or the amount by which) the ventricular rate exceeds the atrial rate by at least a threshold value that varies as a function of the atrial rate, as a function of the ventricular rate, or as a function of the atrial rate and the ventricular rate.

Figure 17:
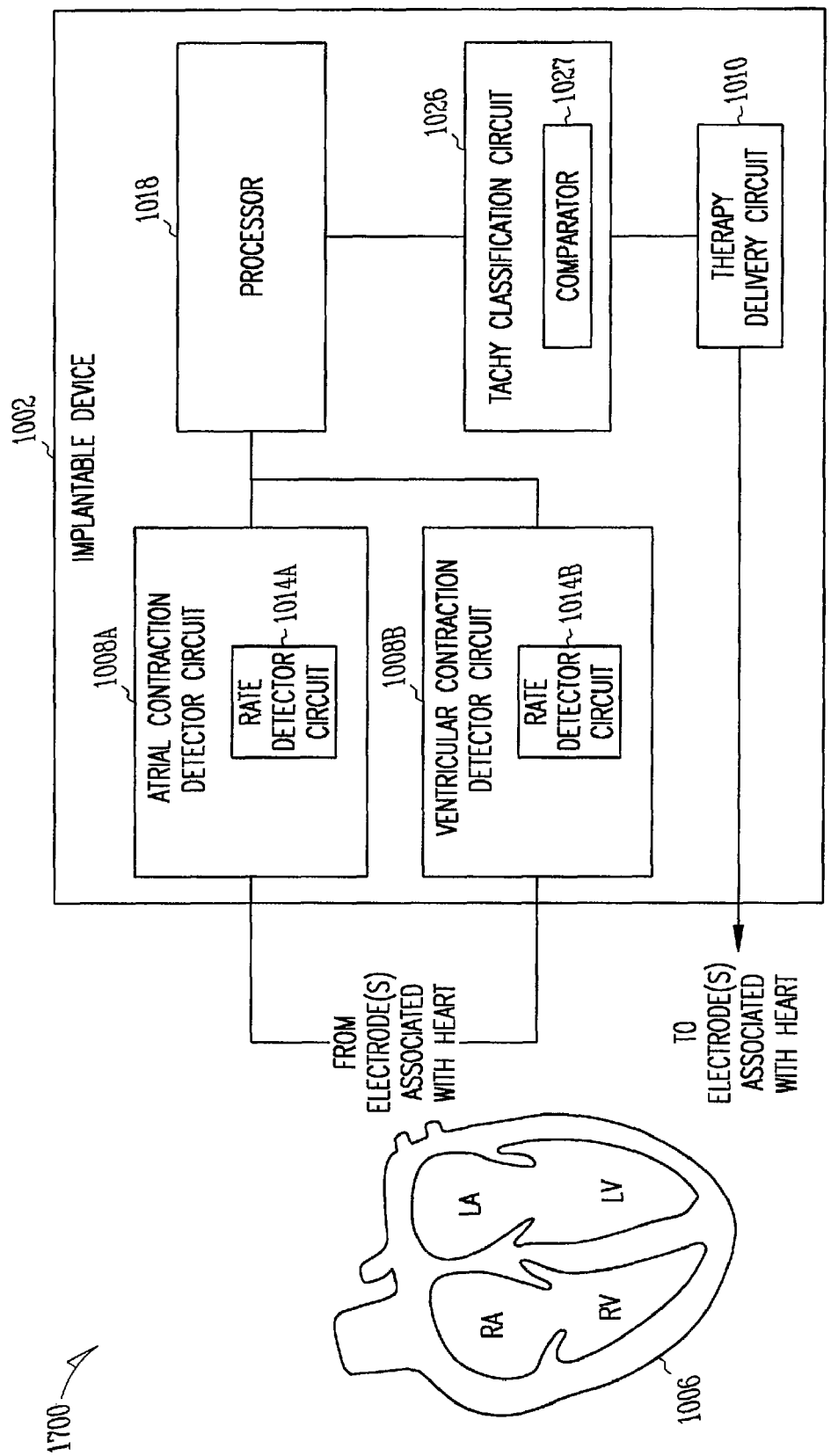
FIG. 17 is a block diagram illustrating generally an example of a system including a tachyarrhythmia classification circuit and a therapy delivery circuit.

FIG. 17 illustrates generally an example of a system 1700 including a cardiac rhythm management (CRM) or other implantable device 1002 that can be coupled to a subject's heart 1006. The system 1700 can include an atrial contraction detector circuit 1008A, a ventricular contraction detector circuit 1008B, a processor 1018, a tachyarrhythmia classification circuit 1026, and a therapy delivery circuit 1010. In FIG. 17, the tachyarrhythmia classification circuit 1026 can include a comparator 1027. In an example, the comparator 1027 can be configured to compare information from at least one of the atrial contraction detector circuit or the ventricular contraction detector circuit to the value of the rhythm discrimination parameter, such as explained below.

In the example of FIG. 17, the therapy delivery circuit 1010 is coupled to the tachyarrhythmia classification circuit 1026. In an example, the therapy delivery circuit 1010 can be configured to deliver an anti-tachyarrhythmia therapy using information from the tachyarrhythmia classification circuit 1026, such as if the tachyarrhythmia classification circuit 1026 classifies the tachyarrhythmia as a ventricular tachyarrhythmia.

Figures 18, 19:
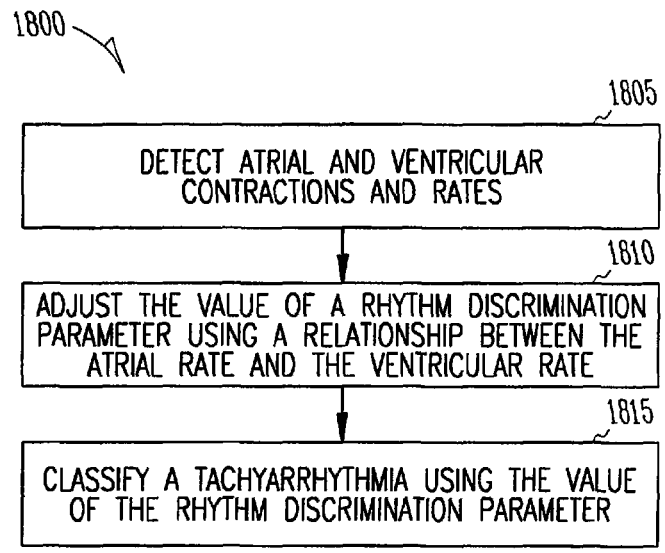
FIG. 18 is a flow chart illustrating generally an example of tachyarrhythmia classification.
FIG. 19 is a flow chart illustrating generally an example of tachyarrhythmia classification using morphology correlation.

FIG. 18 illustrates generally an example of a method 1800 including adjusting the value of a rhythm discrimination parameter using a relationship between a detected atrial rate and a detected ventricular rate.

At 1805, atrial contractions, an atrial rate, ventricular contractions, and a ventricular rate of a heart are detected. In an example, the detecting the atrial and ventricular rates include detecting atrial and ventricular intervals, respectively. In certain examples, the atrial contractions can be detected using the atrial contraction detector circuit 1008A, the atrial rates can be detected using the atrial rate detector circuit 1014A, the ventricular contractions can be detected using the ventricular contraction detector circuit 1008B, and the ventricular rates can be detected using the ventricular rate detector circuit 1014B.

At 1810, the value of a rhythm discrimination parameter can be adjusted such as by using a relationship between the atrial rate and the ventricular rate. Adjusting the value of the rhythm discrimination parameter can improve the specificity or the sensitivity of the rhythm discrimination, increase the efficacy of therapy or therapy delivery, or decrease the amount of unnecessary shocks. In an example, the value of the rhythm discrimination parameter can be increased or decreased depending on the amount by which the ventricular rate exceeds the atrial rate. In an example, as the amount by which the ventricular rate exceeds the atrial rate increases, the likelihood of a specific cardiac rhythm can increase. Thus, the value of the rhythm discrimination parameter can be adjusted to account for the increased likelihood. For example, as the amount by which the ventricular rate exceeds the atrial rate increases, at least one of the "stability" variance threshold, the "onset" rate progression threshold, or the morphology correlation threshold can be decreased. This can make it more likely that the arrhythmia condition will be declared.

In another example, the value of the rhythm discrimination parameter can be increased or decreased depending on the amount by which the atrial rate exceeds the ventricular rate. In an example, the value of the rhythm discrimination parameter can be adjusted (e.g., increased or decreased) using a linear function of the relationship between the atrial rate and the ventricular rate. In other examples, the value can be adjusted using a nonlinear function of the relationship between the atrial rate and the ventricular rate. In an example, the adjusting the value of the rhythm discrimination parameter can include establishing its initial value.

In another example, at 1810, the value of the rhythm discrimination parameter can be adjusted using at least one of the atrial rate or the ventricular rate (e.g., using the atrial rate, using the ventricular rate, or using the atrial rate and the ventricular rate) such as in addition to using the relationship between the atrial rate and the ventricular rate. In an example, the value of the rhythm discrimination parameter can be adjusted using information about the amount by which the ventricular rate exceeds the atrial rate as a function of at least one of the atrial rate or the ventricular rate. For example, as the amount by which the ventricular rate exceeds the atrial rate as a function of the ventricular rate increases, at least one of the "stability" variance threshold, the "onset" rate progression threshold, or the morphology correlation threshold can be decreased. In another example, the value of the rhythm discrimination parameter can be adjusted using information about the amount by which the atrial rate exceeds the ventricular rate as a function of at least one of the atrial rate or the ventricular rate.

In another example, at 1810, the value of the rhythm discrimination parameter can be adjusted using information about whether the ventricular rate exceeds the atrial rate by at least a threshold value that varies as a function of at least one of the atrial rate or the ventricular rate. For example, if the ventricular rate exceeds the atrial rate by a threshold that varies as a function of the ventricular rate, at least one of the "stability" variance threshold, the "onset" rate progression threshold, or the morphology correlation threshold can be decreased. In another example, the value of the rhythm discrimination parameter can be adjusted using information about whether the atrial rate exceeds the ventricular rate by at least a threshold value that varies as a function of at least one of the atrial rate or the ventricular rate. In an example, the value of the rhythm discrimination parameter can be adjusted using the processor 1018.

At 1815, a tachyarrhythmia can be classified (e.g., classified as a ventricular tachyarrhythmia, a supraventricular tachyarrhythmia, an atrial tachyarrhythmia, etc.) using the value of the rhythm discrimination parameter. In an example, the tachyarrhythmia can be classified using the tachyarrhythmia classification circuit 1026. The classification can be provided to a human user or an automated process.

In an example, information from at least one of the detected atrial contractions or the detected ventricular contractions can be compared to the value of the rhythm discrimination parameter, and the tachyarrhythmia can be classified using the results of the comparison. In an example, the information from the at least one of the detected atrial contractions or the detected ventricular contractions can include information from the detected atrial rate, the detected ventricular rate, the detected atrial interval, or the detected ventricular interval. In certain examples, the tachyarrhythmia can be classified using the tachyarrhythmia classification circuit 1026, or the information can be compared to the value of the rhythm discrimination parameter using the comparator 1027.

In certain examples, the information from the at least one of the detected atrial contractions or the detected ventricular contractions can include information about the variance of at least one of the detected atrial contractions or the detected ventricular contractions, information about the change in at least one of the atrial rate, the ventricular rate, the atrial interval, or the ventricular interval (e.g., information about the increase in the atrial rate, information about the increase in the ventricular rate, information about the decrease in the atrial interval, information about the decrease in the ventricular interval, etc.), information about the correlation between at least a portion of at least one of the atrial contraction or the ventricular contraction and a template, or other information relating to a rhythm discrimination parameter.

FIG. 19 illustrates generally an example of a method 1900 including adjusting a morphology correlation threshold using a relationship between a detected atrial rate and a detected ventricular rate, determining a morphology correlation value between a ventricular contraction signal and a template, and classifying a tachyarrhythmia using the morphology correlation value and the morphology correlation threshold.

At 1905, atrial contractions, an atrial rate, ventricular contractions, and a ventricular rate of a heart are detected. In an example, the detecting the atrial and ventricular rates include detecting atrial and ventricular intervals, respectively. In certain examples, the atrial contractions can be detected using the atrial contraction detector circuit 1008A, the atrial rates can be detected using the atrial rate detector circuit 1014A, the ventricular contractions can be detected using the ventricular contraction detector circuit 1008B, and the ventricular rates can be detected using the ventricular rate detector circuit 1014B.

At 1910, a ventricular contraction signal is provided. The ventricular contraction signal is generally a signal indicative of the detected ventricular contraction. In certain examples, the ventricular contraction signal can be provided using the ventricular contraction detector circuit 1008B or the ventricular contraction signal can be provided using the processor 1018.

At 1915, a morphology correlation threshold can be adjusted using a relationship between the atrial rate and the ventricular rate. In an example, as the amount by which the ventricular rate exceeds the atrial rate increases, the morphology correlation threshold can be decreased. In another example, as the amount by which the ventricular rate exceeds the atrial rate as a function of the ventricular rate increases, the morphology correlation threshold can be decreased. In another example, if the ventricular rate exceeds the atrial rate by a threshold that varies as a function of the ventricular rate, then the morphology correlation threshold can be decreased. In an example, the value of the rhythm discrimination parameter can be adjusted using the processor 1018.

At 1920, a morphology correlation value between the ventricular contraction signal and a template can be determined. Generally, the ventricular contraction signal can be compared to the template, such as by using waveform morphology, with the results of the comparison (e.g., the degree of similarity or dissimilarity) being quantified with the morphology correlation value. In certain examples, the morphology correlation value can be determined using the processor 1018 or the tachyarrhythmia classification circuit 1026.

At 1925, a tachyarrhythmia can be classified using the morphology correlation value and the morphology correlation threshold that is adjustable using the relationship between the atrial rate and the ventricular rate. Generally, the tachyarrhythmia can be classified using a comparison of the morphology correlation value and the morphology correlation threshold. In an example, the tachyarrhythmia can be classified using the tachyarrhythmia classification circuit 1026.

Figure 20:
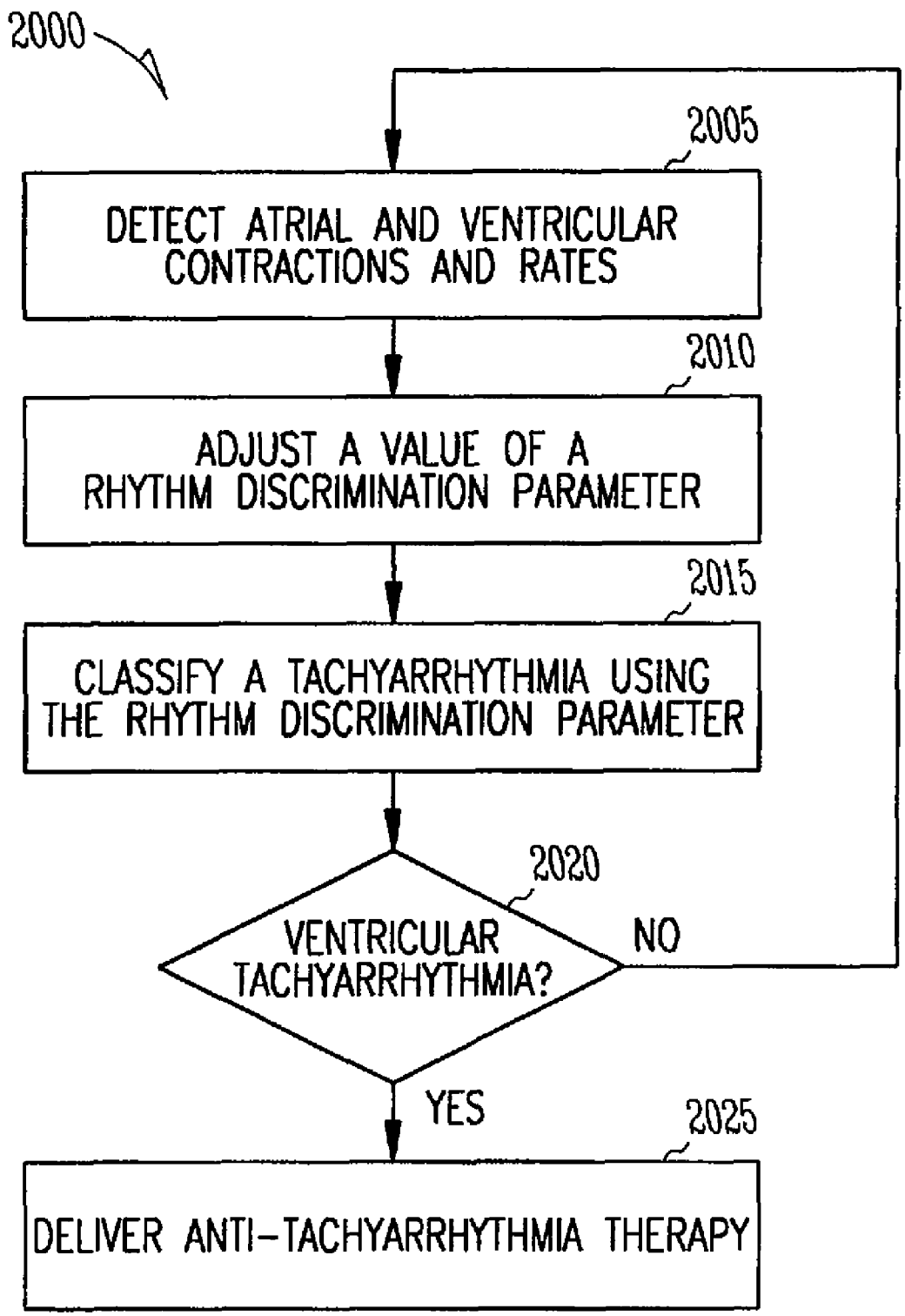
FIG. 20 is a flow chart illustrating generally an example of tachyarrhythmia classification and anti-tachyarrhythmia therapy delivery.

FIG. 20 illustrates generally an example of a method 2000 including adjusting a value of a rhythm discrimination parameter, classifying a tachyarrhythmia using the rhythm discrimination parameter, and delivering an anti-tachyarrhythmia therapy.

At 2005, atrial contractions, an atrial rate, ventricular contractions, and a ventricular rate of a heart are detected. In an example, the detecting the atrial and ventricular rates include detecting atrial and ventricular intervals, respectively. In certain examples, the atrial contractions can be detected using the atrial contraction detector circuit 1008A, the atrial rates can be detected using the atrial rate detector circuit 1014A, the ventricular contractions can be detected using the ventricular contraction detector circuit 1008B, and the ventricular rates can be detected using the ventricular rate detector circuit 1014B.

At 2010, a value of a rhythm discrimination parameter can be adjusted, such as by using a relationship between the atrial rate and the ventricular rate. In other examples, the rhythm discrimination parameter can be adjusted using other criteria, such as by using at least one of the atrial rate or the ventricular rate in addition to using the relationship between the atrial rate and the ventricular rate. In an example, the value of the rhythm discrimination parameter can be adjusted using the processor 1018.

At 2015, a tachyarrhythmia can be classified using the rhythm discrimination parameter. In an example, the tachyarrhythmia can be classified using the tachyarrhythmia classification circuit 1026.

At 2020, if, at 2015, a ventricular tachyarrhythmia is not classified, then process flow returns to 2005. At 2020, if, at 2015, a ventricular tachyarrhythmia is classified, then, at 2025, an anti-tachyarrhythmia therapy can be delivered.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "of" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
    an atrial contraction detector circuit, including an atrial rate detector circuit to detect an atrial rate between atrial contractions of a heart;
    a ventricular contraction detector circuit, including a ventricular rate detector circuit to detect a ventricular rate between ventricular contractions of the heart;
    a tachyarrhythmia classification circuit, configured to classify a tachyarrhythmia using a rhythm discrimination parameter having a value; and
    a processor, coupled to the atrial and ventricular contraction detector circuits and the tachyarrhythmia classification circuit, the processor configured to:
        determine a relationship between the atrial rate and the ventricular rate including comparing a difference between the atrial rate and the ventricular rate to a threshold value to determine whether the atrial rate is substantially equal to the ventricular rate; and
        when the difference between the atrial rate and the ventricular rate exceeds the threshold value thereby indicating that the atrial rate is not substantially equal to the ventricular rate, adjust the value of the rhythm discrimination parameter using the relationship between the atrial rate and the ventricular rate, including adjusting the value of the rhythm discrimination parameter using both of (1) information about whether the atrial rate exceeds the ventricular rate or vice-versa; and (2) a magnitude of the difference between the atrial rate and the ventricular rate.

2. The system of claim 1, wherein the processor is configured to adjust the value of the rhythm discrimination parameter using at least one of the atrial rate or the ventricular rate in addition to using the relationship between the atrial rate and the ventricular rate.

3. The system of claim 2, wherein the processor is configured to adjust the value of the rhythm discrimination parameter using information about the amount that the ventricular rate exceeds the atrial rate as a function of at least one of the atrial rate or the ventricular rate.

4. The system of claim 3, wherein the processor is configured to adjust the value of the rhythm discrimination parameter using information about whether the ventricular rate exceeds the atrial rate by a threshold value, wherein the threshold value varies as a function of at least one of the atrial rate or the ventricular rate.

5. The system of claim 1, wherein the atrial rate is represented by an atrial interval between atrial contractions and the ventricular rate is represented by a ventricular interval between ventricular contractions.

6. The system of claim 1, wherein the tachyarrhythmia classification circuit includes a comparator configured to compare information from at least one of the atrial contraction detector circuit or the ventricular contraction detector circuit to the value of the rhythm discrimination parameter, and the tachyarrhythmia classification circuit is configured to classify the tachyarrhythmia using the results of the comparison.

7. The system of claim 1, wherein the rhythm discrimination parameter includes at least one of stability, onset, or morphology correlation.

8. The system of claim 7, wherein the rhythm discrimination parameter includes stability and the value of the rhythm discrimination parameter includes a variance threshold.

9. The system of claim 8, wherein the ventricular contraction detector circuit is configured to detect a ventricular contraction and provide a ventricular contraction signal, and the rhythm discrimination parameter includes morphology correlation between the ventricular contraction signal and a template, and the value of the rhythm discrimination parameter includes a morphology correlation threshold value.

10. The system of claim 7, wherein the rhythm discrimination parameter includes onset and the value of the rhythm discrimination parameter includes a rate progression threshold.

11. The system of claim 1, wherein the ventricular contraction detector circuit is configured to detect a ventricular contraction and provide a ventricular contraction signal, and the rhythm discrimination parameter includes morphology correlation and the value of the rhythm discrimination parameter includes a morphology correlation threshold between the ventricular contraction signal and a template.

12. The system of claim 11, wherein the template includes at least one of a normal sinus rhythm ventricular contraction template or a tachyarrhythmia ventricular contraction template.

13. The system of claim 1, including a therapy delivery circuit, configured to deliver an anti-tachyarrhythmia therapy if the tachyarrhythmia classification circuit classifies the tachyarrhythmia as a ventricular tachyarrhythmia.

14. A system comprising:
    means for detecting atrial contractions of a heart and an atrial rate between the detected atrial contractions;
    means for detecting ventricular contractions of the heart and a ventricular rate between the detected ventricular contractions;
    means for classifying a tachyarrhythmia using a rhythm discrimination parameter having a value;
    means for determining a relationship between the atrial rate and the ventricular rate including comparing a difference between the atrial rate and the ventricular rate to a threshold value to determine whether the atrial rate is substantially equal to the ventricular rate; and means for adjusting, when the difference between the atrial rate and the ventricular rate exceeds the threshold value thereby indicating that the atrial rate is not substantially equal to the ventricular rate, the value of the rhythm discrimination parameter using the relationship between the atrial rate and the ventricular rate, including adjusting the value of the rhythm discrimination parameter using both of (1) information about whether the atrial rate exceeds the ventricular rate or vice-versa; and (2) a magnitude of the difference between the atrial rate and the ventricular rate.

15. A method comprising:

detecting atrial contractions of a heart and an atrial rate between the detected atrial contractions;

detecting ventricular contractions of the heart and a ventricular rate between the detected ventricular contractions;

classifying a tachyarrhythmia using a rhythm discrimination parameter having a value;

determining a relationship between the atrial rate and the ventricular rate including comparing a difference between the atrial rate and the ventricular rate to a threshold value to determine whether the atrial rate is substantially equal to the ventricular rate; and when the difference between the atrial rate and the ventricular rate exceeds the threshold value, adjusting the value of the rhythm discrimination parameter using the relationship between the atrial rate and the ventricular rate, including adjusting the value of the rhythm discrimination parameter using both of (1) information about whether the atrial rate exceeds the ventricular rate or vice-versa; and (2) a magnitude of the difference between the atrial rate and the ventricular rate.

16. The method of claim 15, wherein the adjusting the value of the rhythm discrimination parameter includes using at least one of the atrial rate or the ventricular rate in addition to using the relationship between the atrial rate and the ventricular rate.

17. The method of claim 16, wherein the adjusting the value of the rhythm discrimination parameter includes using information about the amount that the ventricular rate exceeds the atrial rate as a function of at least one of the atrial rate or the ventricular rate.

18. The method of claim 17, wherein the adjusting the value of the rhythm discrimination parameter includes using information about whether the ventricular rate exceeds the atrial rate by a threshold value that varies as a function of at least one of the atrial rate or the ventricular rate.

19. The method of claim 15, wherein the detecting the atrial rate includes detecting an atrial interval between atrial contractions and the detecting the ventricular rate includes detecting a ventricular interval between ventricular contractions.

20. The method of claim 15, including:

comparing information from at least one of the detected atrial contractions or the detected ventricular contractions to the value of the rhythm discrimination parameter; and wherein the classifying the tachyarrhythmia includes using the results of the comparison.

21. The method of claim 15, wherein the classifying the tachyarrhythmia using the rhythm discrimination parameter includes classifying the tachyarrhythmia using at least one of stability, onset, or morphology correlation.

22. The method of claim 21, wherein the classifying the tachyarrhythmia using the rhythm discrimination parameter having a value includes classifying the tachyarrhythmia using stability having a variance threshold.

23. The method of claim 21, wherein the classifying the tachyarrhythmia using the rhythm discrimination parameter having a value includes classifying the tachyarrhythmia using onset having a rate progression threshold.

24. The method of claim 15, including:

providing a ventricular contraction signal using at least one detected ventricular contraction; and wherein the classifying the tachyarrhythmia using the rhythm discrimination parameter having the value includes using morphology correlation having a morphology correlation threshold.

25. The method of claim 24, wherein the using morphology correlation having the morphology correlation threshold includes determining a morphology correlation value between the ventricular contraction signal and a template and comparing the determined morphology correlation value to the morphology correlation threshold.

26. The method of claim 25, wherein the template includes at least one of a normal sinus rhythm ventricular contraction template or a tachyarrhythmia ventricular contraction template.

27. The method of claim 15, including delivering an anti-tachyarrhythmia therapy if the tachyarrhythmia is classified as a ventricular tachyarrhythmia.

* * * * *